US009480533B2

(12) United States Patent
Devengenzo et al.

(10) Patent No.: US 9,480,533 B2
(45) Date of Patent: Nov. 1, 2016

(54) TELESCOPING INSERTION AXIS OF A ROBOTIC SURGICAL SYSTEM

(71) Applicant: Intuitive Surgical Operations, Inc., Sunnyvale, CA (US)

(72) Inventors: Roman L. Devengenzo, Santa Clara, CA (US); Thomas G. Cooper, Menlo Park, CA (US); Bruce Schena, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 352 days.

(21) Appl. No.: 14/149,360

(22) Filed: Jan. 7, 2014

(65) Prior Publication Data
US 2014/0163581 A1    Jun. 12, 2014

Related U.S. Application Data

(63) Continuation of application No. 13/454,925, filed on Apr. 24, 2012, now Pat. No. 8,641,700, which is a continuation of application No. 11/613,800, filed on Dec. 20, 2006, now Pat. No. 8,182,470.

(60) Provisional application No. 60/752,755, filed on Dec. 20, 2005.

(51) Int. Cl.
*A61B 19/00* (2006.01)
*B25J 15/04* (2006.01)
*A61B 17/00* (2006.01)

(52) U.S. Cl.
CPC .......... *A61B 19/2203* (2013.01); *A61B 34/30* (2016.02); *A61B 34/37* (2016.02); *A61B 34/71* (2016.02); *B25J 15/04* (2013.01); *A61B 90/361* (2016.02); *A61B 2017/00477* (2013.01); *A61B 2034/305* (2016.02); *A61B 2046/234* (2016.02); *Y10T 74/20305* (2015.01)

(58) Field of Classification Search
CPC .. A61B 19/22; A61B 19/2203; A61B 34/30; A61B 2034/305
USPC ...................................... 606/1, 130
See application file for complete search history.

(56) References Cited

U.S. PATENT DOCUMENTS

| 4,547,119 A | 10/1985 | Chance et al. |
| 4,549,839 A | 10/1985 | Glachet et al. |

(Continued)

FOREIGN PATENT DOCUMENTS

| EP | 0595291 A1 | 5/1994 |
| EP | 1433431 A1 | 6/2004 |

(Continued)

OTHER PUBLICATIONS

Co-pending U.S. Appl. No. 60/752,755, filed Dec. 20, 2005.

(Continued)

*Primary Examiner* — William Thomson
*Assistant Examiner* — Jeffrey Lipitz

(57) ABSTRACT

A telescopic insertion axis, a robotic surgical system including the telescopic insertion axis, and a method of instrument insertion are provided. In one embodiment, a telescopic insertion axis includes a base link operably coupled to a distal end of a manipulator arm, and a carriage link movably coupled to the base link along a lengthwise axis, the carriage link including an instrument interface.

20 Claims, 25 Drawing Sheets

(56) References Cited

U.S. PATENT DOCUMENTS

| | | |
|---|---|---|
| 5,372,147 A | 12/1994 | Lathrop, Jr. et al. |
| 5,931,832 A | 8/1999 | Jensen |
| 5,970,980 A | 10/1999 | Adair |
| 6,132,368 A | 10/2000 | Cooper |
| 6,246,200 B1 | 6/2001 | Blumenkranz et al. |
| 6,331,181 B1 | 12/2001 | Tierney et al. |
| 6,491,701 B2 | 12/2002 | Tierney et al. |
| 6,659,939 B2 | 12/2003 | Moll et al. |
| 6,770,081 B1 | 8/2004 | Cooper et al. |
| 7,524,320 B2 | 4/2009 | Tierney et al. |
| 7,666,191 B2 | 2/2010 | Orban, III |
| 7,727,244 B2 | 6/2010 | Orban, III et al. |
| 7,955,322 B2 | 6/2011 | Devengenzo et al. |
| 7,963,913 B2 | 6/2011 | Devengenzo et al. |
| 8,182,469 B2 | 5/2012 | Anderson et al. |
| 8,182,470 B2 | 5/2012 | Devengenzo et al. |
| 8,641,700 B2 | 2/2014 | Devengenzo et al. |
| 2003/0167061 A1 | 9/2003 | Schlegel et al. |
| 2003/0216715 A1 | 11/2003 | Moll et al. |
| 2005/0253607 A1 | 11/2005 | Kimoto |
| 2006/0167440 A1 | 7/2006 | Cooper et al. |
| 2006/0235436 A1 | 10/2006 | Anderson et al. |
| 2007/0142824 A1 | 6/2007 | Devengenzo et al. |
| 2007/0142969 A1 | 6/2007 | Devengenzo et al. |
| 2007/0239105 A1 | 10/2007 | Weitzner et al. |

FOREIGN PATENT DOCUMENTS

| | | |
|---|---|---|
| WO | WO-0134017 A2 | 5/2001 |
| WO | WO-03009069 A1 | 1/2003 |
| WO | WO-2007005555 A2 | 1/2007 |

OTHER PUBLICATIONS

PCT/US06/48710 International Search Report and Written Opinion of the International Searching Authority, mailed May 16, 2007, 10 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

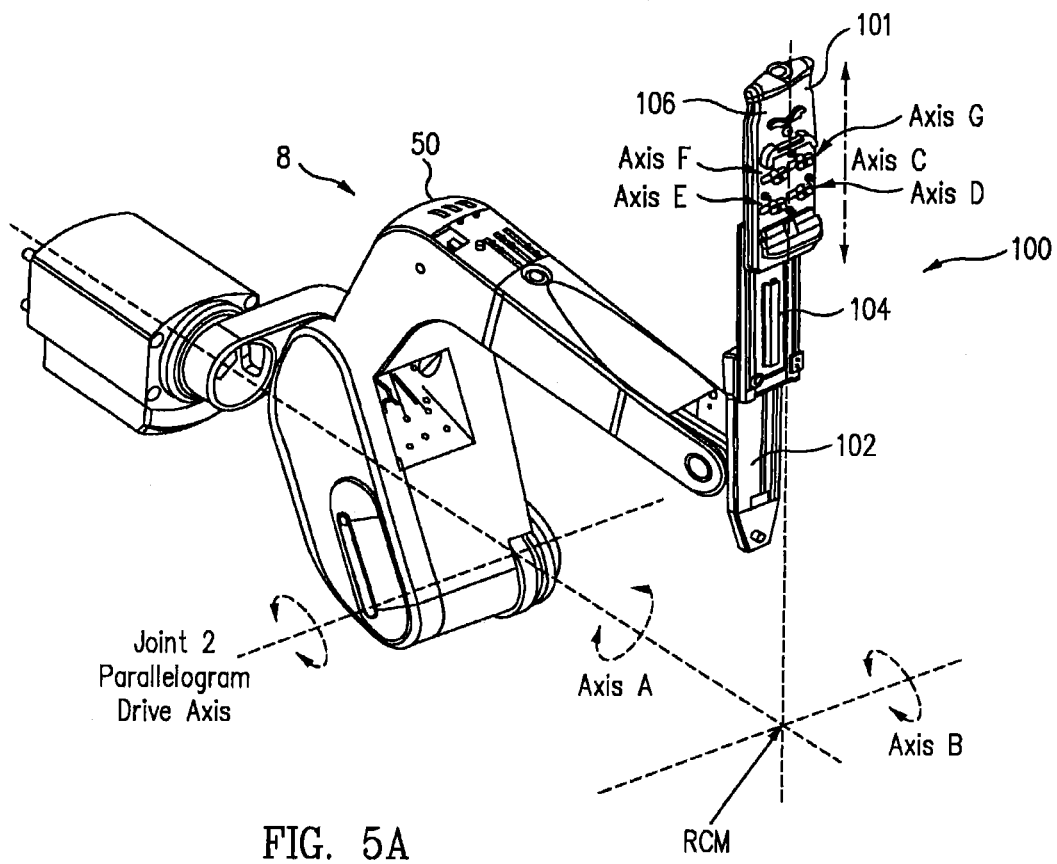
FIG. 5A
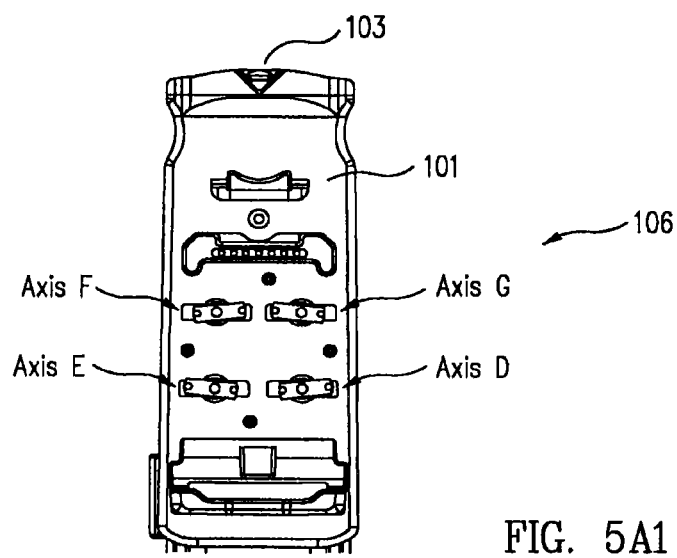
FIG. 5A1

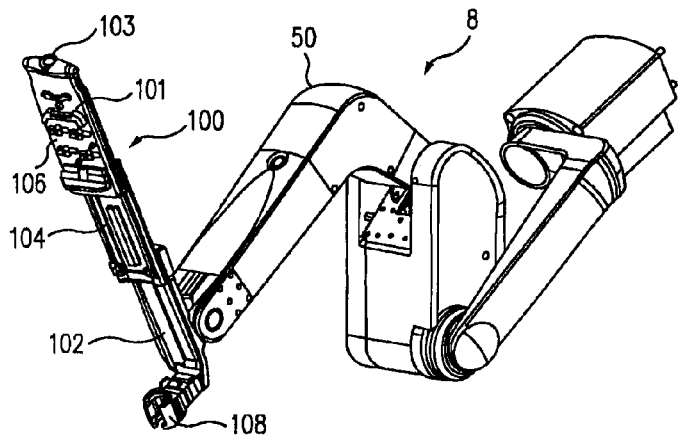
FIG. 5B
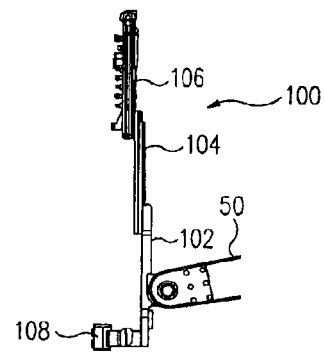
FIG. 5B1
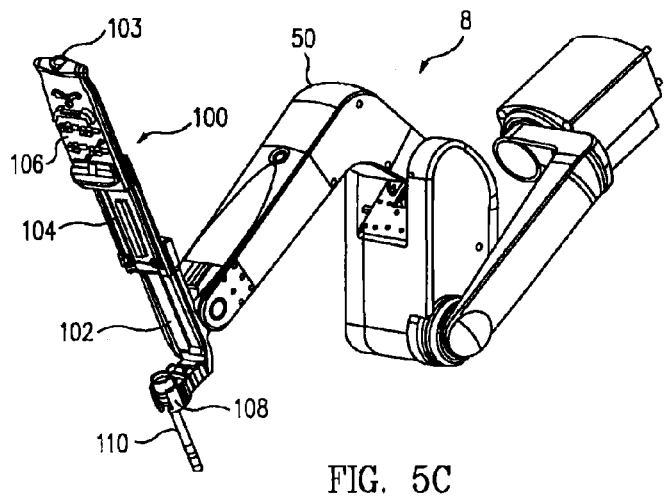
FIG. 5C
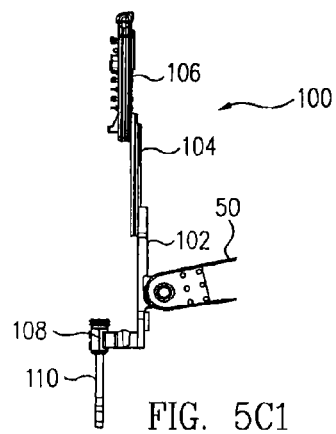
FIG. 5C1

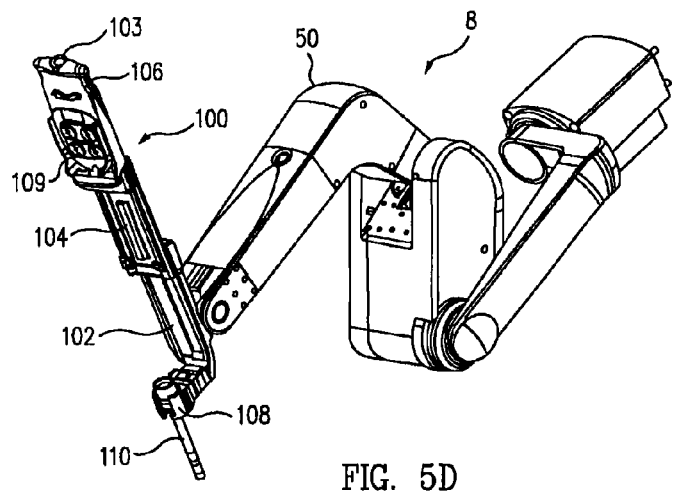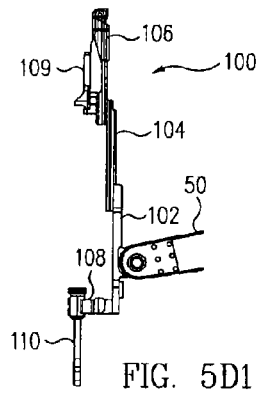
FIG. 5D          FIG. 5D1
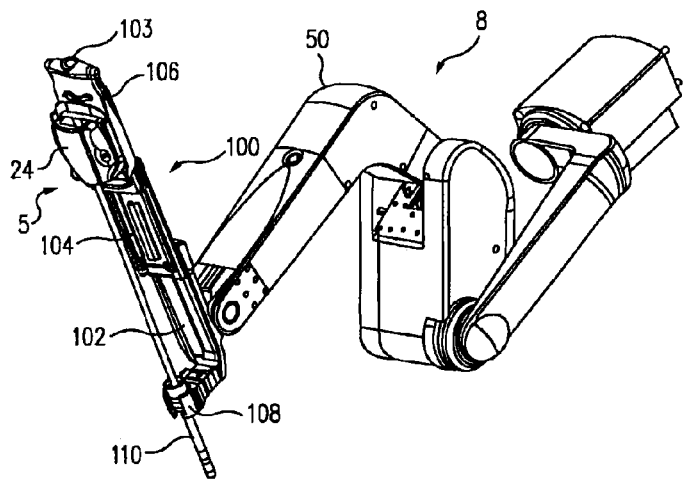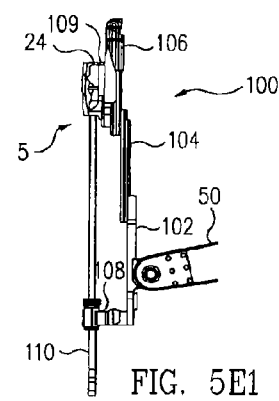
FIG. 5E          FIG. 5E1

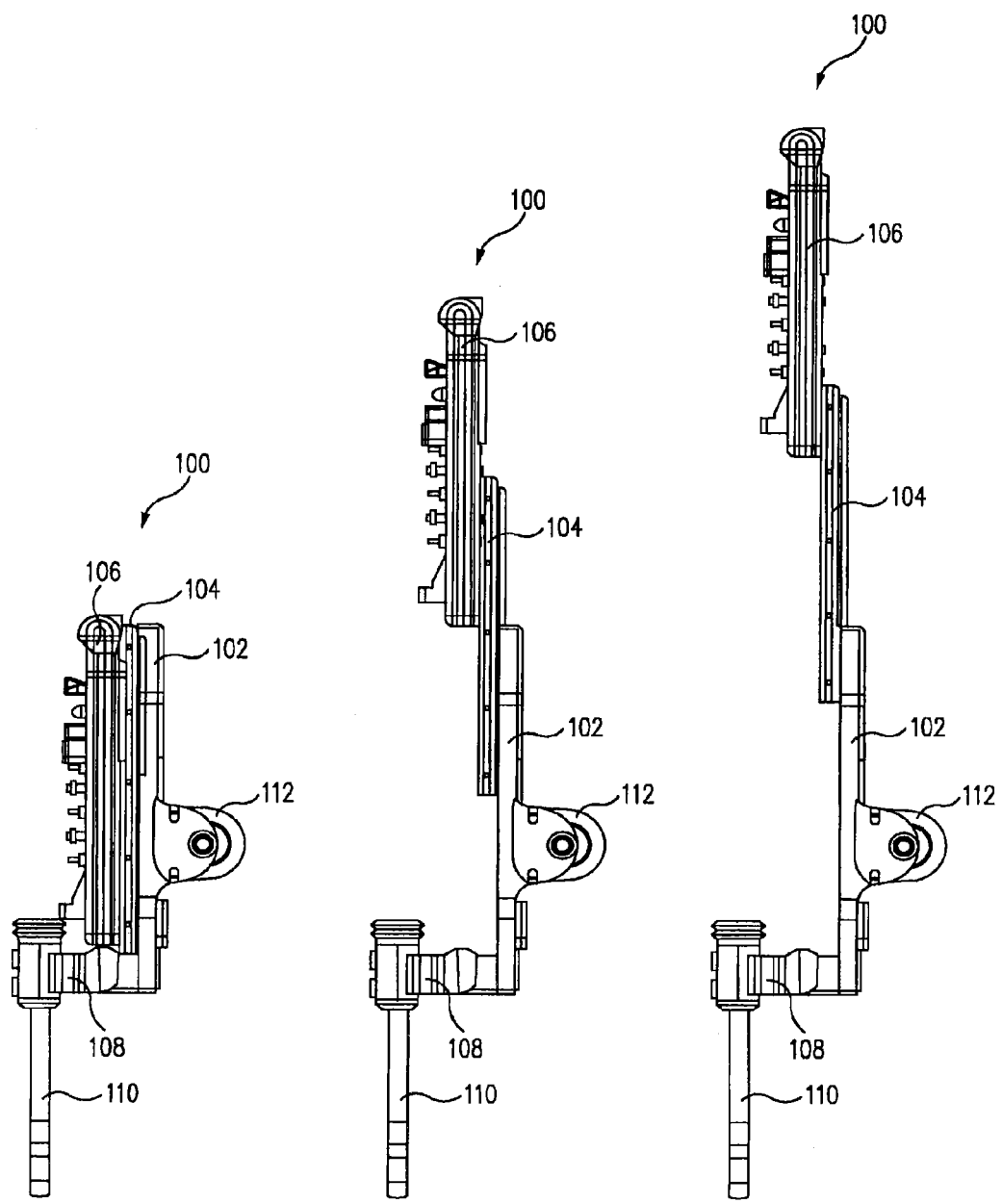
FIG. 6A1   FIG. 6B1   FIG. 6C1

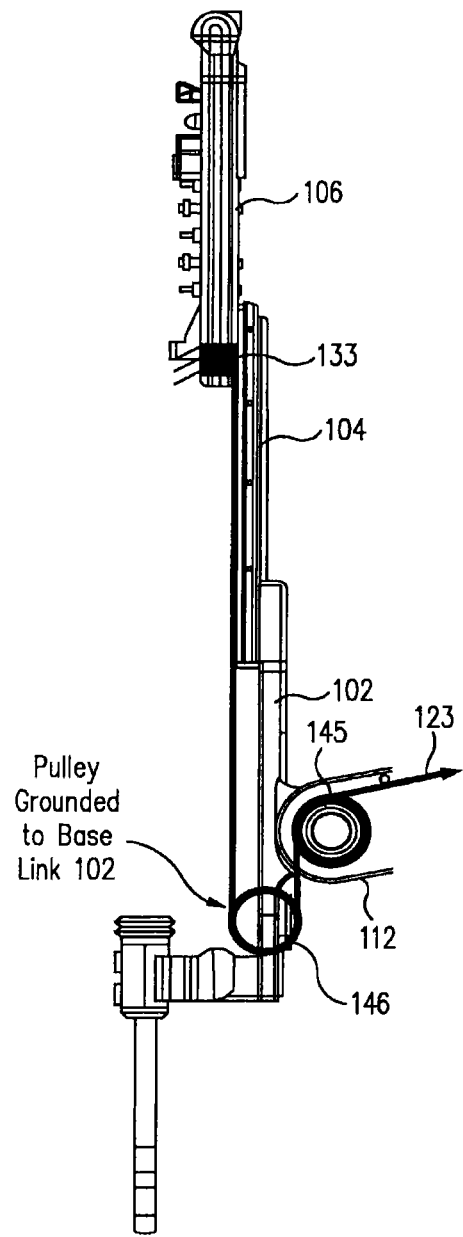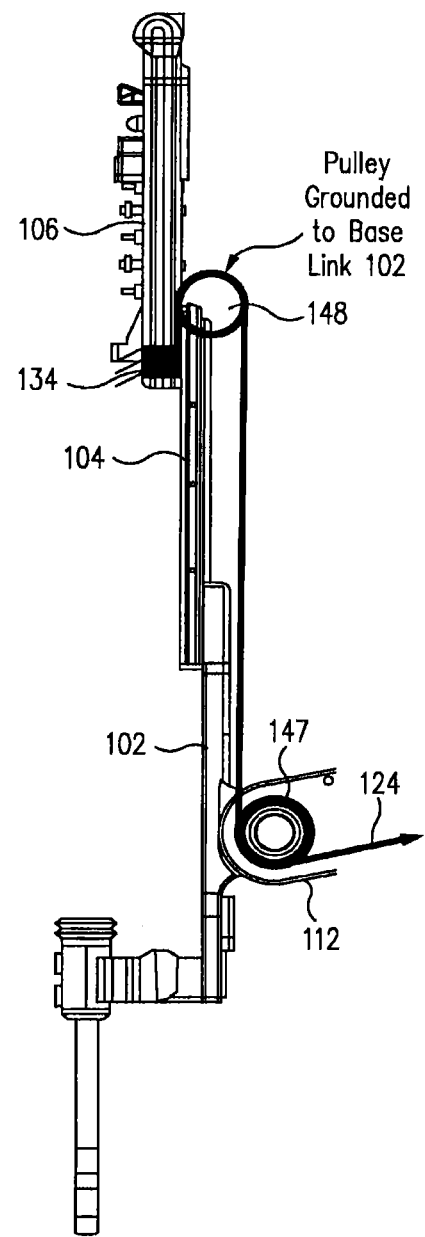
FIG. 11C
FIG. 11D

TELESCOPING INSERTION AXIS OF A ROBOTIC SURGICAL SYSTEM

CROSS-REFERENCE TO RELATED APPLICATIONS

This application is a continuation of U.S. patent application Ser. No. 13/454,925 filed on Apr. 24, 2012, which is a continuation of U.S. patent application Ser. No. 11/613,800 filed on Dec. 20, 2006, now U.S. Pat. No. 8,182,470, which claims the benefit of U.S. Provisional Application 60/752,755 filed on Dec. 20, 2005, the full disclosures of which (including all references incorporated by reference therein) are incorporated herein by reference in their entirety.

This application is related to U.S. application Ser. No. 11/613,578, filed Dec. 20, 2006, entitled "Cable Tensioning In A Robotic Surgical System", U.S. application Ser. No. 11/556,484, filed Nov. 3, 2006, entitled "Indicator For Tool State and Communication In a Multi-Arm Robotic Telesurgery", U.S. application Ser. No. 11/613,695, filed Dec. 20, 2006, entitled "Instrument Interface In A Robotic Surgical System", and application Ser. No. 11/613,915, filed Dec. 20, 2006, entitled "Wireless Communication In A Robotic Surgical System", the full disclosures of which (including all references incorporated by reference therein) are incorporated by reference herein for all purposes.

TECHNICAL FIELD

The present invention is generally related to medical and/or robotic devices, systems, and methods.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, may be reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and to avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servomechanically operated instruments.

In robotically-assisted surgery, the surgeon typically operates a master controller to control the motion of surgical instruments at the surgical site from a location that may be remote from the patient (e.g., across the operating room, in a different room, or a completely different building from the patient). The master controller usually includes one or more hand input devices, such as hand-held wrist gimbals, joysticks, exoskeletal gloves or the like, which are operatively coupled to the surgical instruments that are releasably coupled to a patient side surgical manipulator ("the slave"). The master controller controls the instruments' position, orientation, and articulation at the surgical site. The slave is an electro-mechanical assembly which includes a plurality of arms, joints, linkages, servo motors, etc. that are connected together to support and control the surgical instruments. In a surgical procedure, the surgical instruments (including an endoscope) may be introduced directly into an open surgical site or more typically through trocar sleeves into a body cavity. Depending on a surgical procedure, there are available a variety of surgical instruments, such as tissue graspers, needle drivers, electrosurgical cautery probes, etc., to perform various functions for the surgeon, e.g., holding or driving a needle, suturing, grasping a blood vessel, or dissecting, cauterizing or coagulating tissue.

A surgical manipulator assembly may be said to be divided into three main components that include a non-sterile drive and control component, a sterilizable end effector or surgical tool/instrument, and an intermediate connector component. The intermediate connector component includes mechanical elements for coupling the surgical tool with the drive and control component, and for transferring motion from the drive component to the surgical tool.

While telesurgical systems, devices, and methods have proven highly effective and advantageous, still further improvements would be desirable. In general, it would be desirable to provide greater insertion axis stiffness and strength and a larger range of motion. It would also be desirable to reduce the form factor (including width and/or thickness) of the insertion apparatus near the instrument insertion site to enhance visibility for the surgical team as well as to reduce the likelihood of interference between multiple manipulator arms during a procedure.

SUMMARY

The present invention provides a surgical manipulator and system including a telescoping insertion axis controlled and coupled by cables, pulleys, and linear bearings. A method of operating such an assembly or system is also provided.

In accordance with an embodiment of the present invention, an insertion axis of a surgical manipulator is provided, the insertion axis comprising a base link operably coupled to a distal end of a manipulator arm, and a carriage link movably coupled to the base link along a lengthwise axis, the carriage link including an instrument interface.

In accordance with another embodiment of the present invention, a robotic surgical manipulator system is provided, the system comprising a manipulator assembly, including a first link operably coupled to a distal end of a manipulator arm, a second link movably coupled to the first link along a lengthwise axis, and a third link movably coupled to the second link along the lengthwise axis, the third link including an instrument interface. The system further includes an instrument coupled to the third link via the instrument interface, and a processor operably coupled to the manipulator assembly for moving the first, second, and third links relative to one another along the lengthwise axis.

In accordance with yet another embodiment of the present invention, a method of moving a surgical instrument is provided, the method comprising providing a telescoping insertion axis of a robotic manipulator, including a base link operably coupled to a distal end of a manipulator arm, and a carriage link movably coupled to the base link along a lengthwise axis, the carriage link including an instrument interface. The method further includes mounting an instrument on the carriage link via the instrument interface, and moving the base link and the carriage link relative to one another to move the instrument along the lengthwise axis.

Advantageously, the present invention provides one-handed port and instrument clutching, greater insertion axis stiffness and strength, a larger range of motion, and a narrower insertion arm form factor, thereby helping to enable a two-quadrant surgical procedure with a single setup (e.g., colorectal surgery), while also improving manipulator responsiveness, surgical field visibility, and patient safety. Other advantages of the invention are provided. Form factor may include the width and/or thickness of the structure being described.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIGS. 5A-5E and 5B1-5E1 are perspective views and respective side views of a manipulator including a telescopic insertion axis in accordance with an embodiment of the present invention. FIG. 5A1 is a close-up view of a carriage link of the telescopic insertion axis in accordance with an embodiment of the present invention.

FIGS. 6A-6C and 6A1-6C1 are perspective views and respective side views of the insertion axis, an accessory mount (e.g., a cannula mount), and an accessory (e.g., a cannula), the insertion axis being telescoped from a retracted position in FIGS. 6A and 6A1, to an intermediate position in FIGS. 6B and 6B1, and to a fully extended position in FIGS. 6C and 6C1.

FIGS. 11A-11F illustrate different cable and pulley schemes in accordance with embodiments of the present invention, with FIGS. 11A-11D illustrating schemes for the insertion axis drive cables, and FIGS. 11E and 11F illustrating schemes for the wrist cables.

Figure 1:
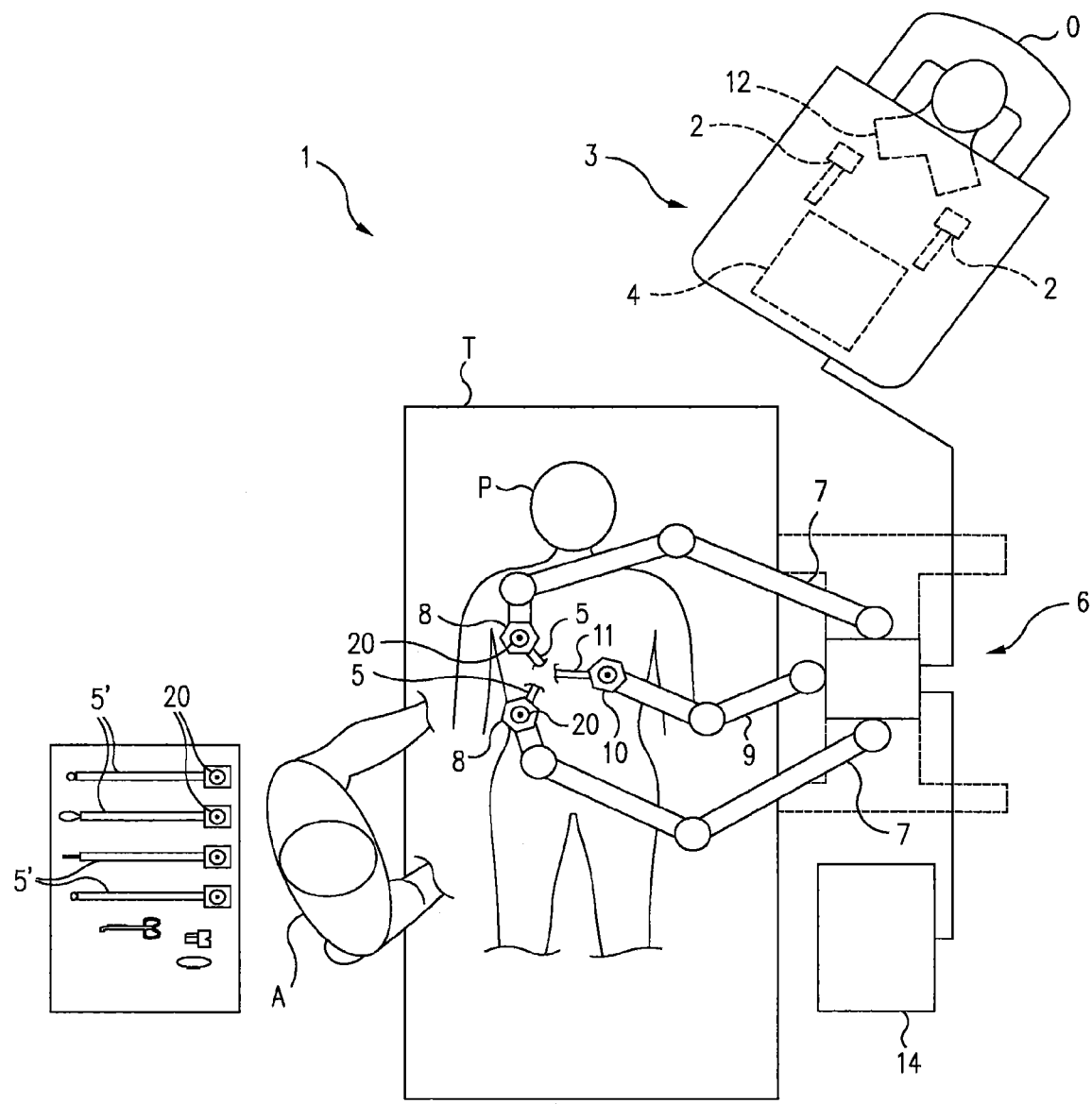
FIG. 1 is a schematic plan view of a portion of an operating theater illustrating a robotic surgical system, including a master surgeon console or workstation for inputting a surgical procedure and a robotic manipulator system for robotically moving surgical instruments at a surgical site within a patient.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention generally provides an improved robotic insertion axis, system, and method for inserting an instrument, and in particular includes a telescopic insertion axis for providing greater stiffness and strength, a larger range of motion, and improved surgical field visibility.

The apparatus, system, and method of the present invention is particularly useful for performing neurosurgical procedures, such as stereotaxy, and endoscopic procedures, such as laparoscopy, arthroscopy, thoracoscopy and the like. Furthermore, the present invention is particularly useful as part of a telerobotic surgical system that allows the surgeon to manipulate the surgical instruments through a servo-mechanism at a location remote from the patient. One example of a robotic surgical system is the da Vinci® S™ surgical system available from Intuitive Surgical, Inc. of Sunnyvale, Calif. A User's Guide for the da Vinci.RTM. S.TM. surgical system is available from Intuitive Surgical, Inc. and is incorporated by reference herein for all purposes.

Figure 2A:
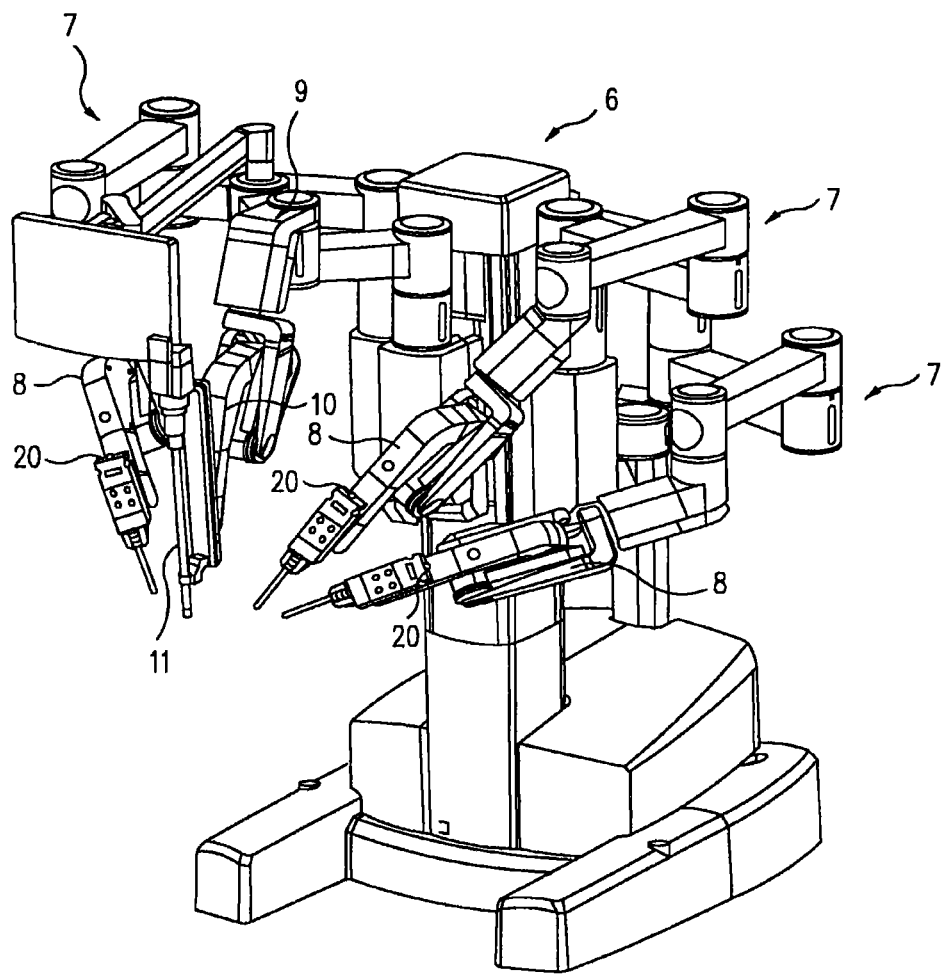
FIGS. 2A and 2B illustrate a perspective view and a front view, respectively, of an embodiment of a manipulator system, including positioning linkages or set up joints which allow a patient side robotic manipulator and/or an endoscope or camera robotic manipulator to be pre-configured for surgery.
Figure 2B:
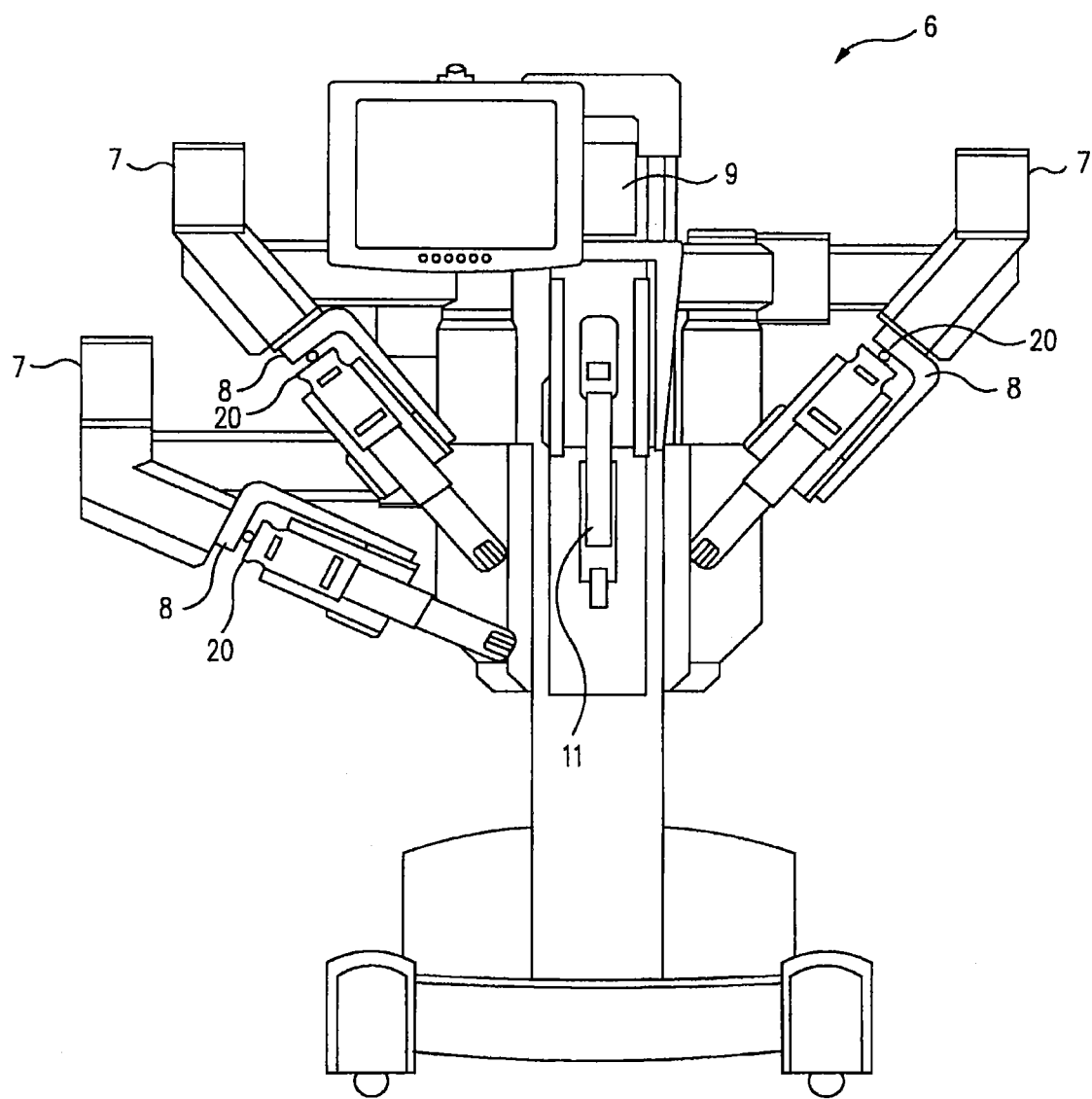
Figure 3:
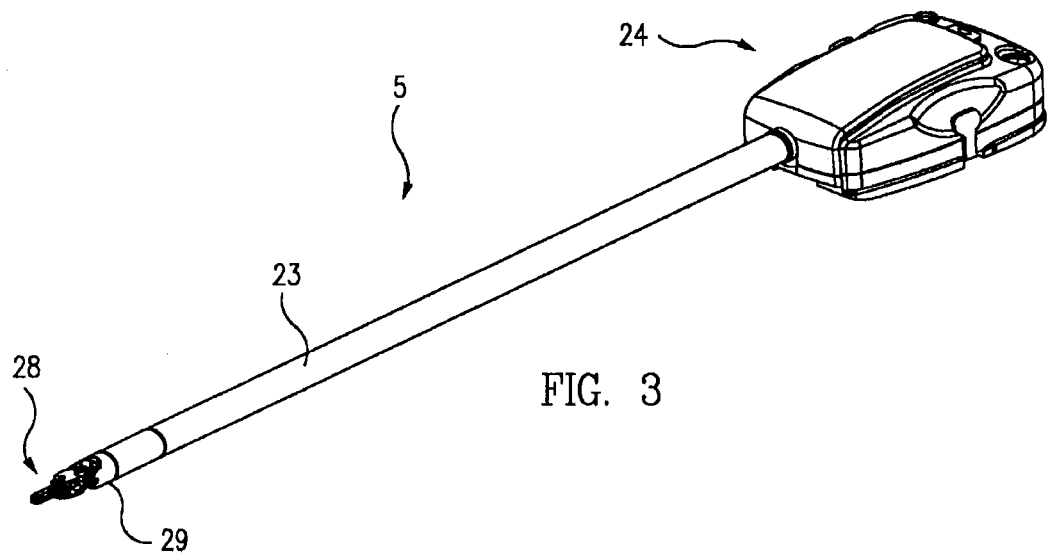
FIG. 3 is a perspective view of an example of a surgical instrument for use in the system of FIG. 1.

FIGS. 1-3 illustrate components of a robotic surgical system 1 for performing minimally invasive robotic surgery. System 1 is similar to that described in more detail in U.S. Pat. No. 6,246,200, the full disclosure of which is incorporated herein by reference. A system operator O (generally a surgeon) performs a minimally invasive surgical procedure on a patient P lying on an operating table T. The system operator O sees images presented by display 12 and manipulates one or more input devices or masters 2 at a surgeon's console 3. In response to the surgeon's input commands, a computer processor 4 of console 3 directs movement of surgical instruments or tools 5, effecting servomechanical movement of the instruments via a robotic patient-side manipulator system 6 (a cart-based system in this example) including joints, linkages, and manipulator arms each having a telescopic insertion axis. In one embodiment, processor 4 correlates the movement of the end effectors of tools 5 so that the motions of the end effectors follow the movements of the input devices in the hands of the system operator O.

Processor 4 will typically include data processing hardware and software, with the software typically comprising machine-readable code. The machine-readable code will embody software programming instructions to implement some or all of the methods described herein. While processor 4 is shown as a single block in the simplified schematic of FIG. 1, the processor may comprise a number of data processing circuits, with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein.

In one example, manipulator system 6 includes at least four robotic manipulator assemblies. Three linkages 7 (mounted at the sides of the cart in this example) support and position manipulators 8 with linkages 7 in general supporting a base of the manipulators 8 at a fixed location during at least a portion of the surgical procedure. Manipulators 8 move surgical tools 5 for robotic manipulation of tissues. One additional linkage 9 (mounted at the center of the cart in this example) supports and positions manipulator 10 which controls the motion of an endoscope/camera probe 11 to capture an image (preferably stereoscopic) of the internal surgical site. The fixable portion of positioning linkages 7, 9 of the patient-side system is sometimes referred to herein as a "set-up arm".

In one example, the image of the internal surgical site is shown to operator O by a stereoscopic display 12 in surgeon's console 3. The internal surgical site is simultaneously shown to assistant A by an assistance display 14.

Assistant A assists in pre-positioning manipulator assemblies 8 and 10 relative to patient P using set-up linkage arms 7, 9; in swapping tools 5 from one or more of the surgical manipulators for alternative surgical tools or instruments 5'; in operating related non-robotic medical instruments and equipment; in manually moving a manipulator assembly so that the associated tool accesses the internal surgical site through a different aperture, and the like.

In general terms, the linkages 7, 9 are used primarily during set-up of patient-side system 6, and typically remain in a fixed configuration during at least a portion of a surgical procedure. Manipulators 8, 10 each comprise a driven linkage which is actively articulated under the direction of surgeon's console 3. Although one or more of the joints of the set-up arm may optionally be driven and robotically controlled, at least some of the set-up arm joints may be configured for manual positioning by assistant A.

Some of the manipulators include a telescopic insertion axis 100 in accordance with an embodiment of the present invention, although in other embodiments, all of the manipulators may include a telescopic insertion axis 100. Telescopic insertion axis 100 allows for movement of mounted instrument 5, via three operably coupled links, in one example, with improved stiffness and strength compared to previous designs, a larger range of motion, and improved dynamic performance and visibility proximate the surgical field for system users (in addition to other advantages), as is described in greater detail below.

For convenience, a manipulator such as manipulator 8 that is supporting a surgical tool used to manipulate tissues is sometimes referred to as a patient-side manipulator (PSM), while a manipulator 10 which controls an image capture or data acquisition device such as endoscope 11 may be referred to as an endoscope-camera manipulator (ECM). The manipulators may optionally actuate, maneuver and control a wide variety of instruments or tools, image capture devices, and the like which are useful for surgery.

Figures 6A, 6B, 6C:
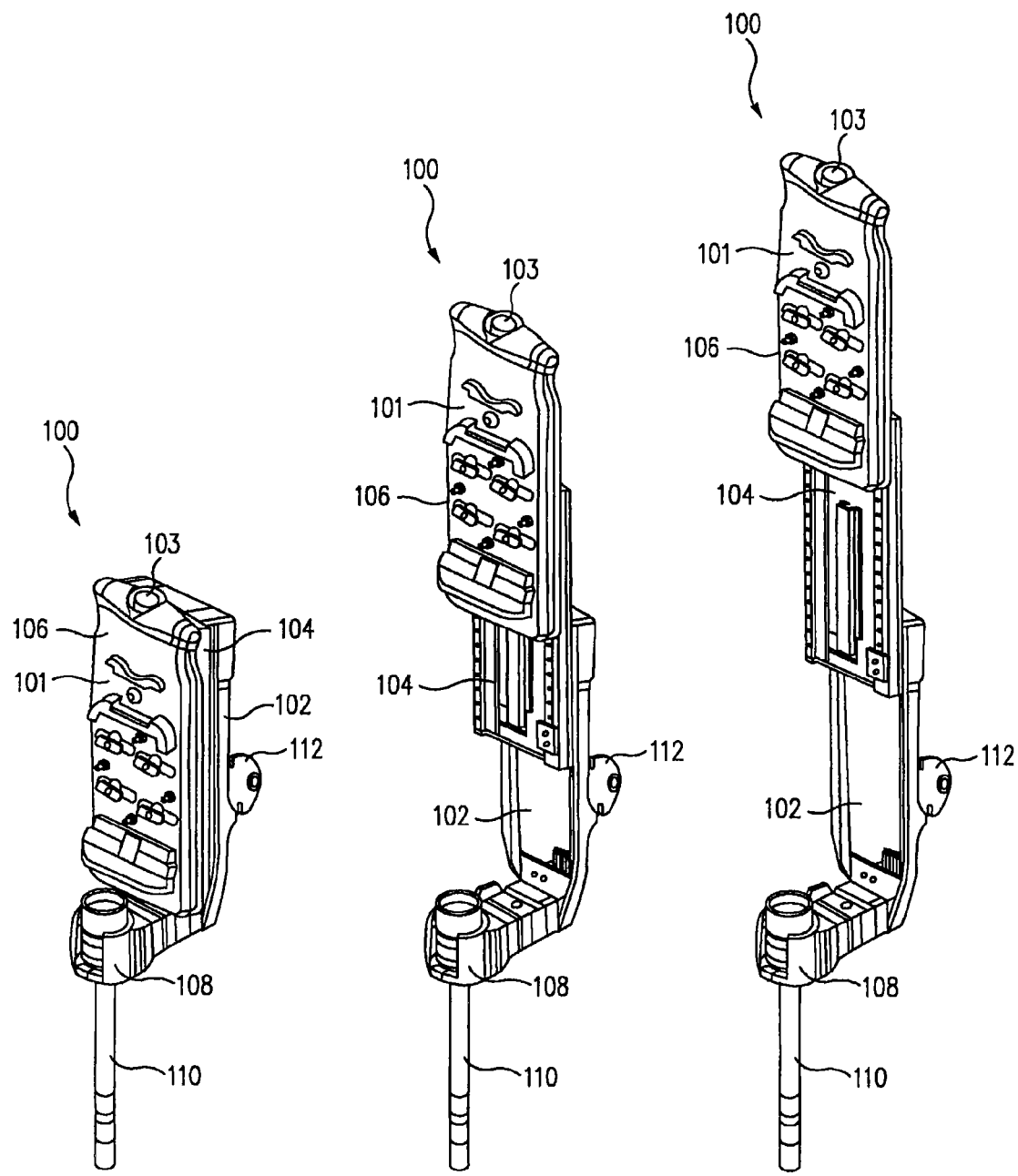

Instruments 5 and endoscope 11 may be manually positioned when setting up for a surgical procedure, when reconfiguring the manipulator system 6 for a different phase of a surgical procedure, when removing and replacing an instrument with an alternate instrument 5', and the like. During such manual reconfiguring of the manipulator assembly by assistant A, the manipulator assembly may be placed in a different mode than is used during master/slave telesurgery, with the manually repositionable mode sometimes being referred to as a clutch mode. The manipulator assembly may change between the tissue manipulation mode and the clutch mode in response to an input such as pushing a button or switch on manipulator 8 (e.g., a clutch button/switch 103 in FIGS. 6A-6C), or some other component to the manipulator assembly, thereby allowing assistant A to change the manipulator mode.

As can be seen in FIGS. 1 and 2A-2B, indicators 20 may be disposed on a manipulator assembly. In this embodiment, indicators 20 are disposed on manipulators 8 near the interface between the manipulators and their mounted tools 5. In alternative embodiments, indicators 20 may instead be disposed on set-up joints 7, 9, on tools 5, elsewhere on manipulators 8, 10, or the like. An example of an indicator is disclosed in U.S. application Ser. No. 11/556,484, filed Nov. 3, 2006, the full disclosure of which (including all references incorporated by reference therein) is incorporated by reference herein for all purposes.

FIG. 3 illustrates a perspective view of an articulated surgical tool or instrument 5. Tool 5 has a proximal housing 24 which interfaces with a tool holder or instrument interface of the manipulator, generally providing a quick release mounting engagement through a sterile adapter or interface, an example of which is disclosed in U.S. patent application Ser. No. 11/314,040, filed Dec. 20, 2005, and U.S. patent application Ser. No. 11/395,418, filed Mar. 31, 2006, which are incorporated by reference herein for all purposes. Tool 5 includes an elongated shaft 23 supporting an end effector 28 relative to proximal housing 24. Proximal housing 24 accepts and transmits drive signals or drive motion between the manipulator 8 and the end effector 28. An articulated wrist 29 may provide two degrees of freedom of motion between end effector 28 and shaft 23, and the shaft may be rotatable relative to proximal housing 24 about the axis of the shaft so as to provide the end effector 28 with three orientational degrees of freedom within the patient's body.

The surgical tool may include a variety of articulated end effectors, such as jaws, scissors, graspers, needle holders, micro-dissectors, staple appliers, tackers, suction irrigation tools, and clip appliers, that may be driven by wire links, eccentric cams, push-rods, or other mechanisms. In addition, the surgical tool may comprise a non-articulated instrument, such as cutting blades, probes, irrigators, catheters or suction orifices. Alternatively, the surgical tool may comprise an electrosurgical probe for ablating, resecting, cutting or coagulating tissue. Examples of applicable adaptors, tools or instruments, and accessories are described in U.S. Pat. Nos. 6,331,181, 6,491,701, and 6,770,081, the full disclosures of which (including disclosures incorporated by reference therein) are incorporated by reference herein for all purposes. Applicable surgical instruments are also commercially available from Intuitive Surgical, Inc. of Sunnyvale, Calif.

Figure 4:
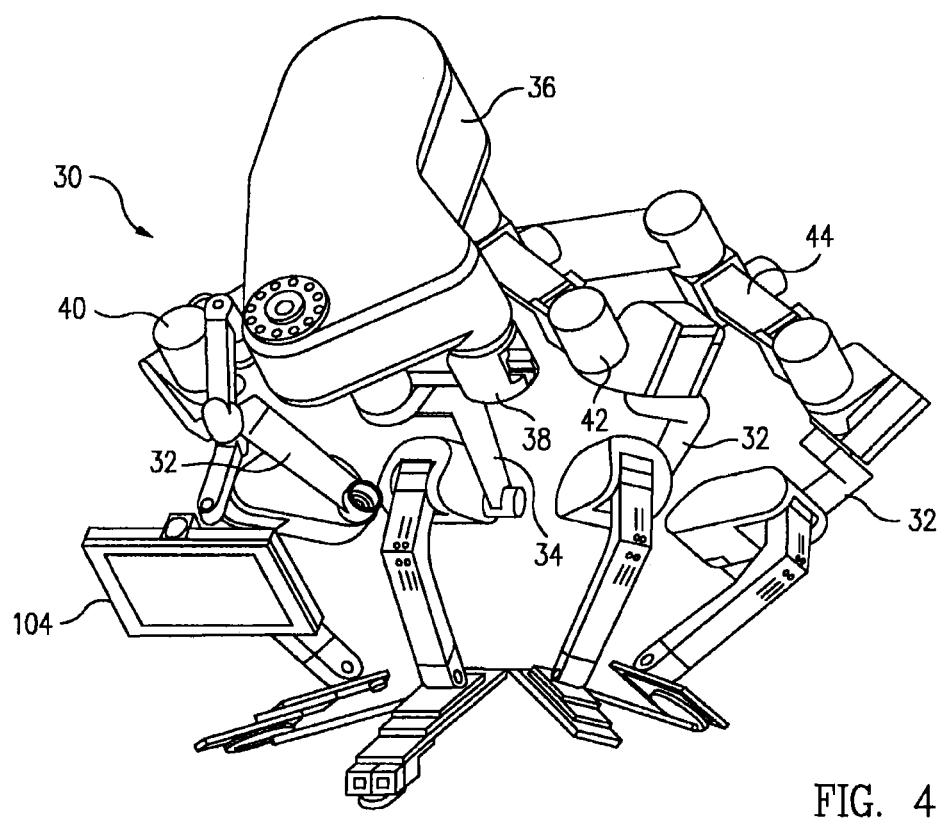
FIG. 4 is a perspective from above of an alternative manipulator system including a plurality of positioning linkages, each supporting a manipulator arm.

Referring now to FIG. 4, a perspective view is illustrated of an alternative modular manipulator support assembly 30 that may be mounted to a ceiling of an operating room. The modular manipulator support 30 aligns and supports a robotic manipulator system relative to a set of desired surgical incision sites in a patient's body. Modular manipulator support 30 generally includes an orientating platform 36 and a plurality of configurable set-up linkage arms 38, 40, 42, 44 that may be coupled to the orienting platform. Each arm movably supports an associated manipulator 32, 34, which in turn movably supports an associated tool or an image capture device. Orienting platform 36 also supports an assistant display 104, which may be used for set-up, instrument changes, viewing of the procedure, and the like. The structures and use of any of the components of modular manipulator support assembly 30 are analogous to those described above regarding manipulator system 6, and are more fully described in co-pending U.S. patent application Ser. No. 11/043,688, filed on Jan. 24, 2005, and entitled "Modular Manipulator Support For Robotic Surgery", the full disclosure of which is incorporated herein by reference. As generally described above, each manipulator 32, 34 of modular manipulator support 30 may also include an insertion axis 100.

Referring now to FIGS. 5A-13B, manipulator 8 including a telescopic insertion axis 100 is shown in more detail in accordance with embodiments of the present invention. The insertion axis of the present invention is comprised of a three-stage telescopic linear axis including three links, in one example, movably coupled to one another via linear bearings, pulleys, and cables, with the links narrowing in width or form factor moving from the proximal link toward the distal link. Advantageously, the present invention provides for one-handed port clutching and one-handed instrument clutching, a larger range of motion, a narrower insertion arm, and greater insertion axis stiffness and strength with reduced inertia as a function of insertion depth, thereby helping to enable a two-quadrant surgery with a single setup (e.g., a colorectal surgery), and providing for more space and visibility near the surgical field. It is noted that although the term "cable" is used in this document, the present invention is not limited to the use of cables and flexible elements may be generally applicable, such as timing belts, chains, etc.

FIGS. 5A-5E and 5B1-5E1 illustrate perspective views and respective side views of manipulator 8 including a manipulator arm 50, and telescopic insertion axis 100 operably coupled to a distal end of arm 50 in accordance with an embodiment of the present invention. Telescopic insertion axis 100 includes a first link or base link 102, a second link or idler link 104 operably coupled to base link 102, and a third link or carriage link 106 operably coupled to idler link 104. FIG. 5A1 is a close-up view of carriage link 106 of the telescopic insertion axis in accordance with an embodiment of the present invention.

Base link 102 is operably coupled to a distal end of manipulator arm 50, and in one example has an accessory clamp 108 attached to a distal end of base link 102. An accessory 110, such as a cannula, may be mounted onto accessory clamp 108. An example of applicable accessory clamps and accessories are disclosed in pending U.S. application Ser. No. 11/240,087, filed Sep. 30, 2005, the full disclosure of which is incorporated by reference herein for all purposes. An example of applicable sterile adaptors and instrument housings are disclosed in U.S. application Ser. No. 11/314,040, filed Dec. 20, 2005 and in U.S. application Ser. No. 11/395,418, filed Mar. 31, 2006, the full disclosures of which are incorporated by reference herein for all purposes.

Carriage link 106 includes an instrument interface 101 for operably coupling to a sterile adaptor 109, that may operably couple to a housing of an instrument (e.g., housing 24 of FIGS. 3 and 5). In one embodiment, the sterile adaptor is part of a drape (FIGS. 14A-14D) that may be draped over the robotic surgical system, and in particular the manipulator system, to establish a sterile barrier between the non-sterile PSM arms and the sterile field of the surgical procedure. An example of an applicable drape and adaptor is disclosed in pending U.S. application Ser. No. 11/240,113, filed Sep. 30, 2005, the full disclosure of which is incorporated by reference herein for all purposes. In other embodiments, the sterile adaptor may be separate from the drape.

Idler link 104 is movably coupled between base link 102 and carriage link 106 to allow the links 102 and 106 to move relative to one another along a lengthwise axis (e.g., axis C) in a telescoping fashion. In one embodiment, link 102 has a narrower form factor than link 104, and link 104 has a narrower form factor than link 106, thus providing for greater visibility near the surgical field. Although the insertion axis described above includes three links operably coupled to one another, the number of links may vary. In particular, the insertion axis of the present invention may include two or more links (e.g., four or more) movably coupled to one another allowing for telescopic movement relative to one another. Additional links allow the retracted assembly to have shorter length but will increase thickness for a given stroke length of the output link.

FIGS. 6A-6C and 6A1-6C1 are perspective views and respective side views, of the insertion axis 100, accessory mount 108 (e.g., a cannula mount), and an accessory 110 (e.g., a cannula) but not including an instrument or an instrument adaptor. The insertion axis 100 is telescoped from a retracted position in FIGS. 6A and 6A1, to an intermediate position in FIGS. 6B and 6B1, and to a fully extended position in FIGS. 6C and 6C1. In one embodiment, the carriage link 106 may translate a distance of about 11.5 inches between the retracted position and the extended position, while the idler carriage 104 may translate a distance of about 5.75 inches.

Motion along axes C through G in manipulator 8, as shown in FIGS. 5A and 5A1, are provided by cables extending at least between the proximal and distal links in accordance with the present invention. The robotic arm can then control a tool or instrument operably coupled to the arm. The cables are a component of a transmission system also including drive pulleys, capstans, idler pulleys, and/or output pulleys, which are driven by electric motors. A pulley bank is located on an underside of base link 102 for passing cables and electrical wires between insertion axis 100 and manipulator arm 50 of manipulator system 6. A plurality of motion feed-throughs, in addition to other elements, may also be provided for transferring motion.

The drive assembly may further include a plurality of drive motors coupled to the arm for rotation therewith. Yaw and pitch motors control the motion of the arm about the A axis and the B axis (FIG. 5A), respectively, and drive motors control the motion of the wrist unit and thus the surgical tool. In one embodiment, four drive motors are mounted proximally in the arm to control four degrees of freedom of the tool mounted distally on the arm (the D, E, F, and G axes). Also, a proximally mounted motor controls the insertion position of the tool distally on the arm (along the C axis). The drive motors will preferably be coupled to encoders and potentiometers (not shown) to enable the servomechanism. Embodiments of the drive assembly, arm, and other applicable parts are described for example in U.S. Pat. Nos. 6,331,181, 6,491,701, and 6,770,081, the full disclosures of which (including disclosures incorporated by reference therein) are incorporated herein by reference for all purposes. The manipulator arm and the drive assembly may also be used with a broad range of positioning devices. A more complete description of a remote center positioning device can be found in U.S. patent application Ser. No. 08/504,301, filed Jul. 20, 1995, now U.S. Pat. No. 5,931,832, the complete disclosure of which is incorporated herein by reference for all purposes.

Figure 7:
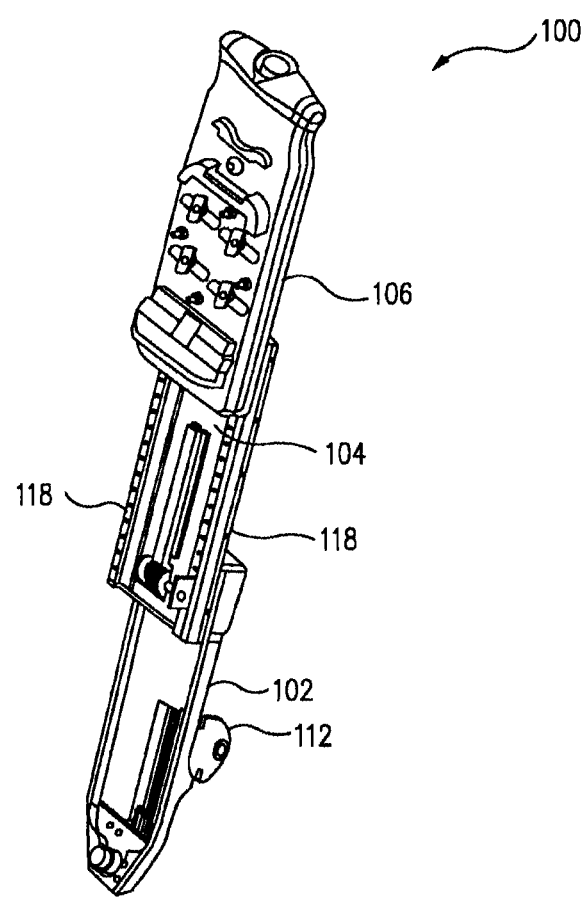
FIG. 7 is a perspective view of the insertion axis at a fully extended position without an accessory mount.
Figure 8A:
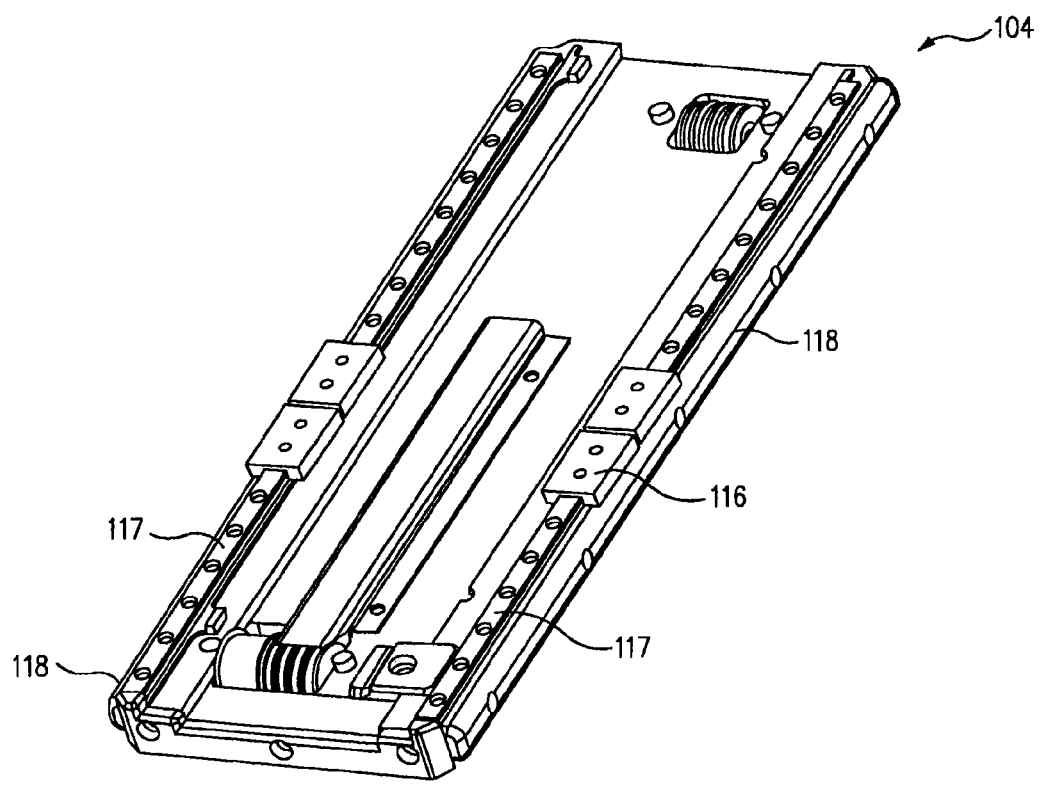
FIGS. 8A and 8B are a perspective view and a top view, respectively, of an idler link of the insertion axis illustrating linear bearings in accordance with an embodiment of the present invention.
Figure 8B:
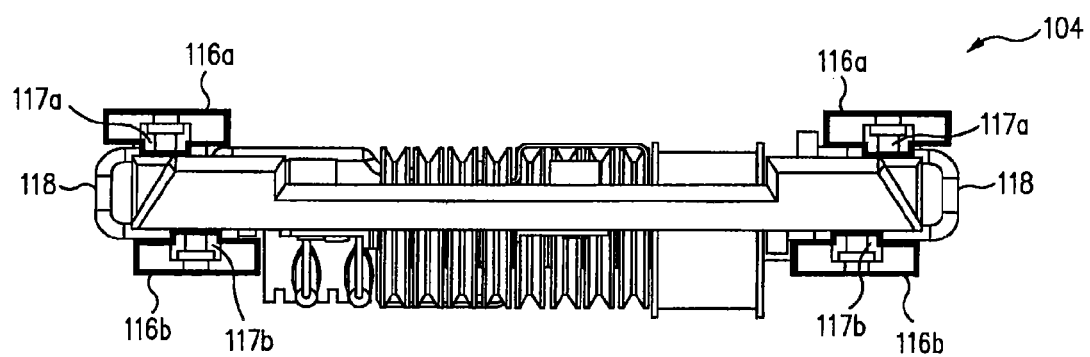
Figure 9A:
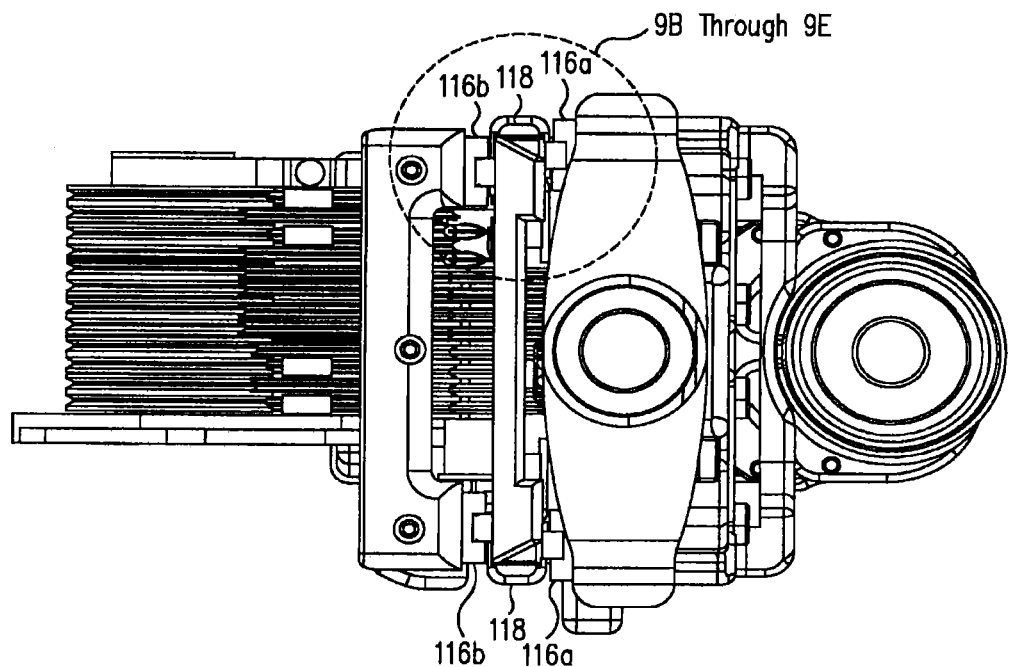
FIGS. 9A-9E illustrate dual rail pressure plates of the insertion axis in accordance with an embodiment of the present invention.
Figure 9B:
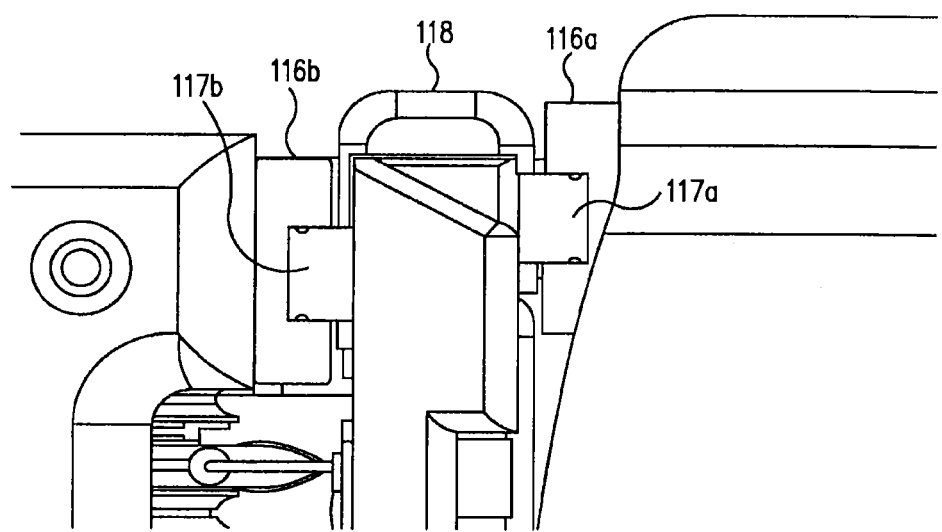
Figure 9C:
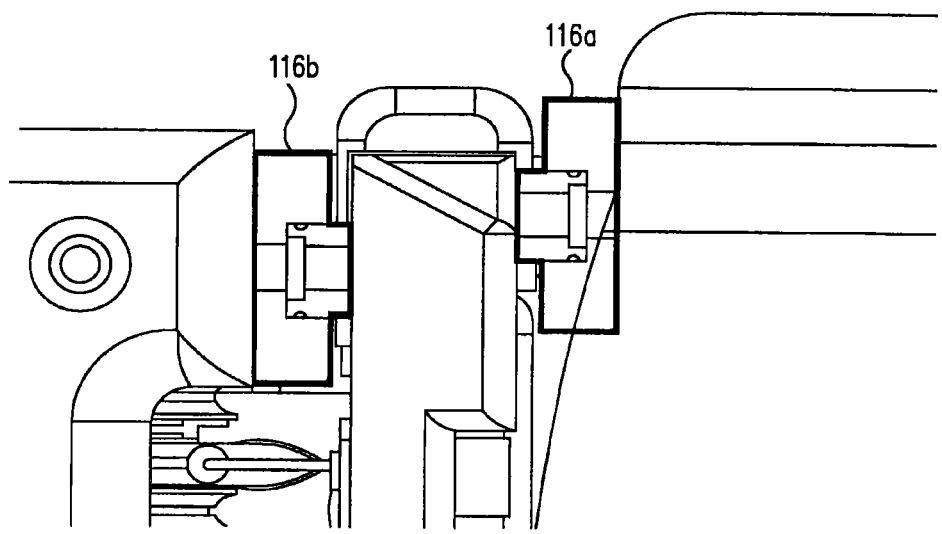
Figure 9D:
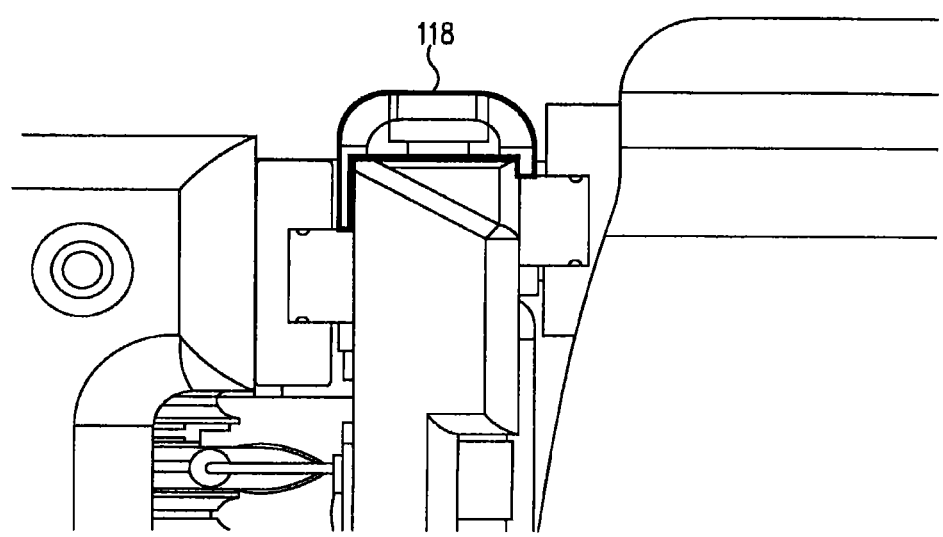
Figure 9E:
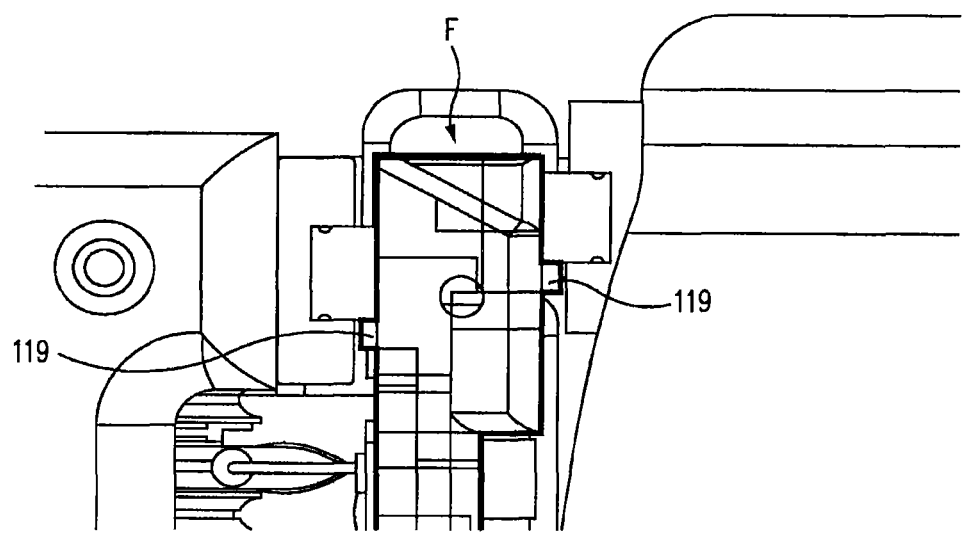

Referring now to FIGS. 7, 8A-8B, and 9A-9E, linear rails, bearings, and dual rail pressure plates for operably moving the links 102, 104, and 106 relative to one another will be described in accordance with an embodiment of the present invention. FIG. 7 illustrates a perspective view of the insertion axis 100 at a fully extended position without the accessory mount. FIGS. 8A and 8B illustrate a perspective view and a front view, respectively, of idler link 104 including linear bearings comprised of slide units 116 and rails 117 in accordance with an embodiment of the present invention. FIGS. 9A-9E illustrate dual rail pressure plates 118 of the idler link in accordance with an embodiment of the present invention.

The links of insertion axis 100 are movably coupled to one another via linear bearings comprised of rails 117 fixably mounted on the top and bottom surfaces of idler link 104. Slide units 116a slidable along rails 117a operably couple links 104 and 106 (see FIGS. 9A-9E), and slide units 116b slidable along rails 117b operably couple links 104 and 102 (see FIGS. 9A-9E), thus allowing the links to translate relative to one another. Although a pair of linear bearings are described herein, it is noted that a single linear bearing may be used to movably couple links of the insertion axis in other embodiments of the present invention.

FIGS. 9A-9E illustrate dual rail pressure plates 118 mounted to idler link 104 in accordance with an embodiment of the present invention. A dual rail pressure plate 118 provides a clamping force (in the direction of arrow F in FIG. 9E) to a pair of linear rails 117a and 117b on each shoulder 119 of link 104, thereby reducing part count while maintaining functionality of the pressure plates and rails.

Figure 10:
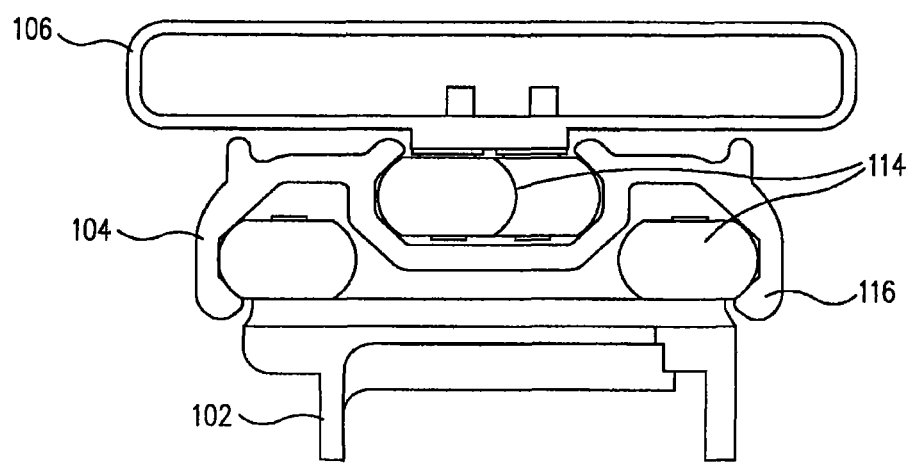
FIG. 10 is a cross-sectional view of the insertion axis, illustrating linear rails and rollers in accordance with another embodiment of the present invention.

In another embodiment, as illustrated in FIG. 10, rollers 114 may be used with linear guide ways 116 for smoothly moving the links 102, 104, and 106 relative to one another along the lengthwise axis of the links. In this embodiment, guide ways 116 are included in link 104 and rollers 114 are included in links 102 and 106. Alternative arrangements of guide ways and rollers are also possible. In yet other embodiments, v-rollers, sliding bushings, ball splines, ball screws, etc., may be used for translating the links relative to one another.

Referring now to FIGS. 11A-11F, different cable and pulley schemes for the insertion axis are provided in accordance with embodiments of the present invention. FIGS. 12A-12C illustrate views of cabling in an insertion link, an idler carriage link, and a carriage link of the insertion axis, respectively, in accordance with an embodiment of the present invention. The drivetrain of insertion axis 100 is comprised of cables (sometimes called wire ropes) that serve two specific purposes.

Figure 11A:
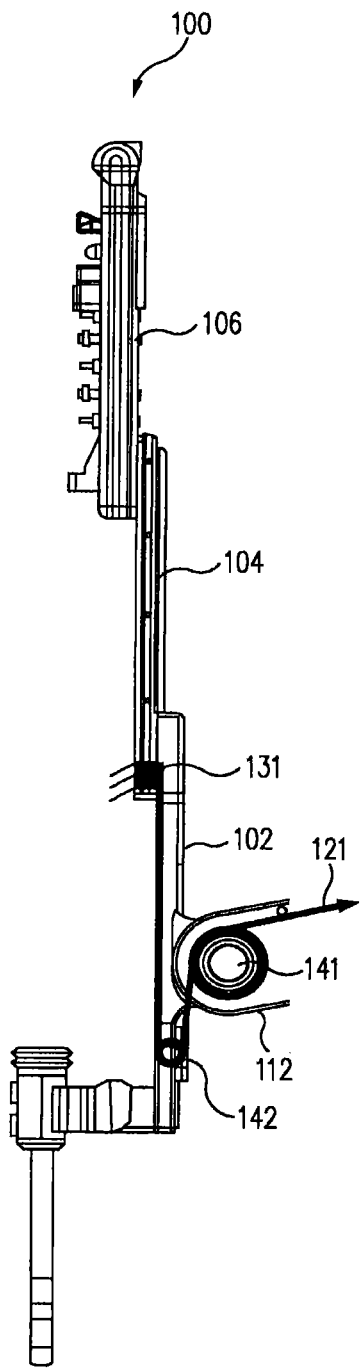
Figure 11B:
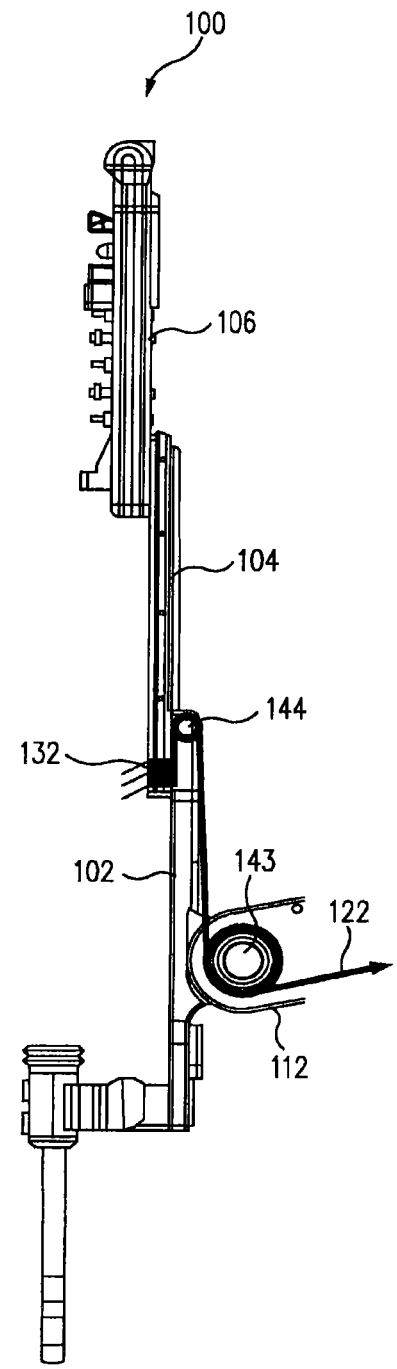
Figure 12A:
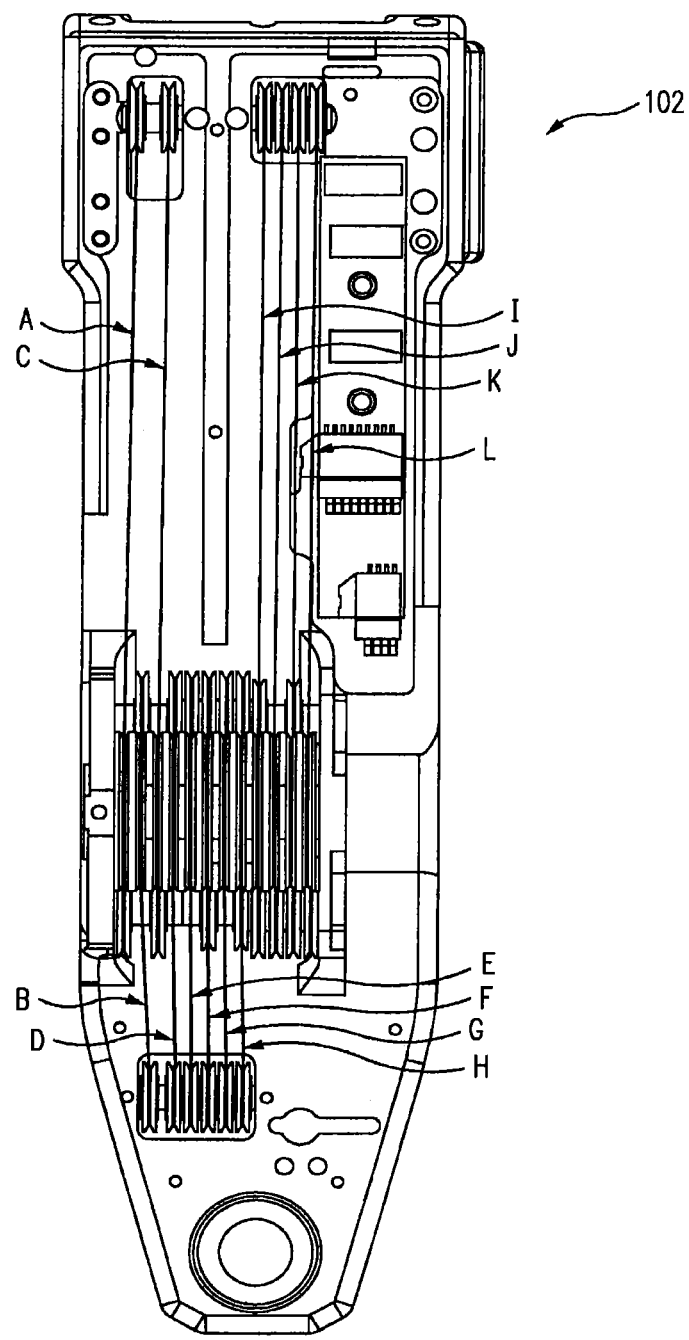
FIGS. 12A-12C illustrate views of cabling in a base link, an idler carriage link, and a carriage link of the insertion axis, respectively, in accordance with an embodiment of the present invention.
Figure 12B:
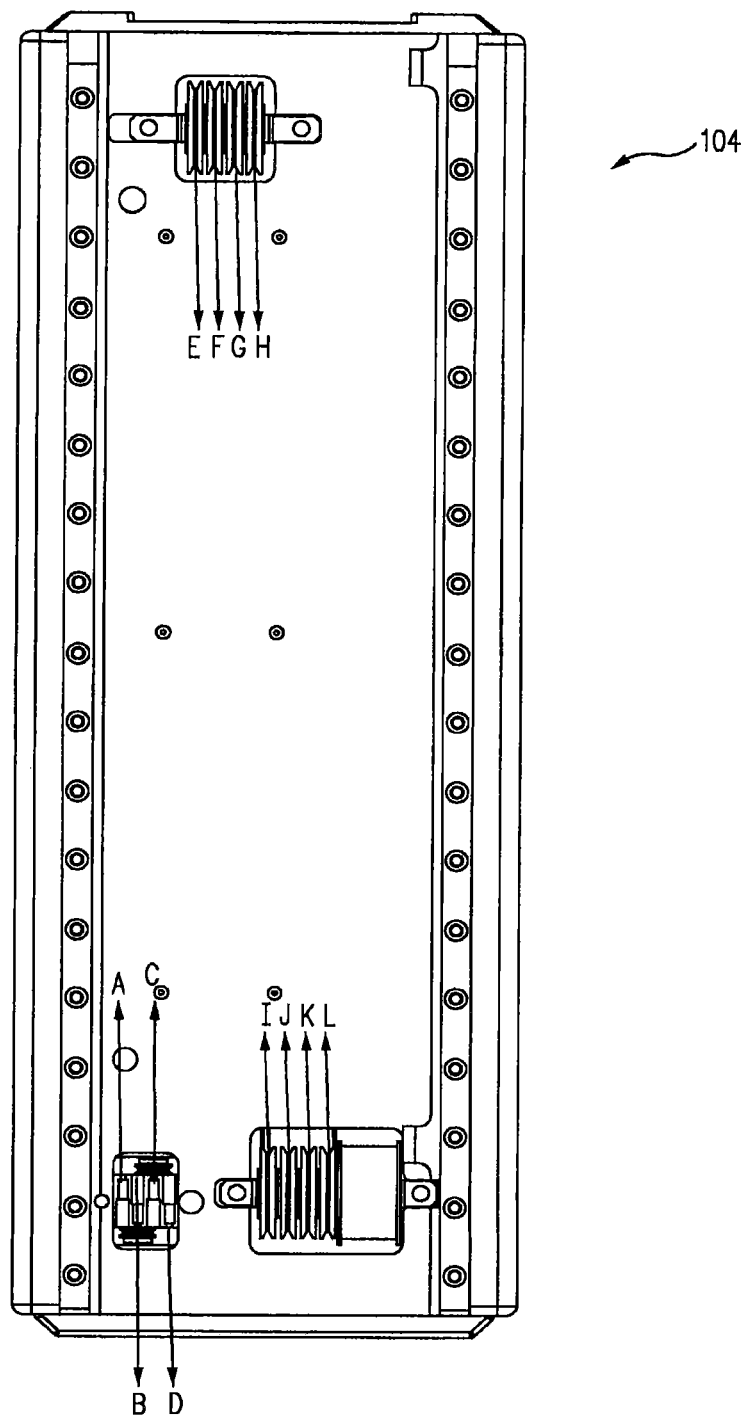
Figure 12C:
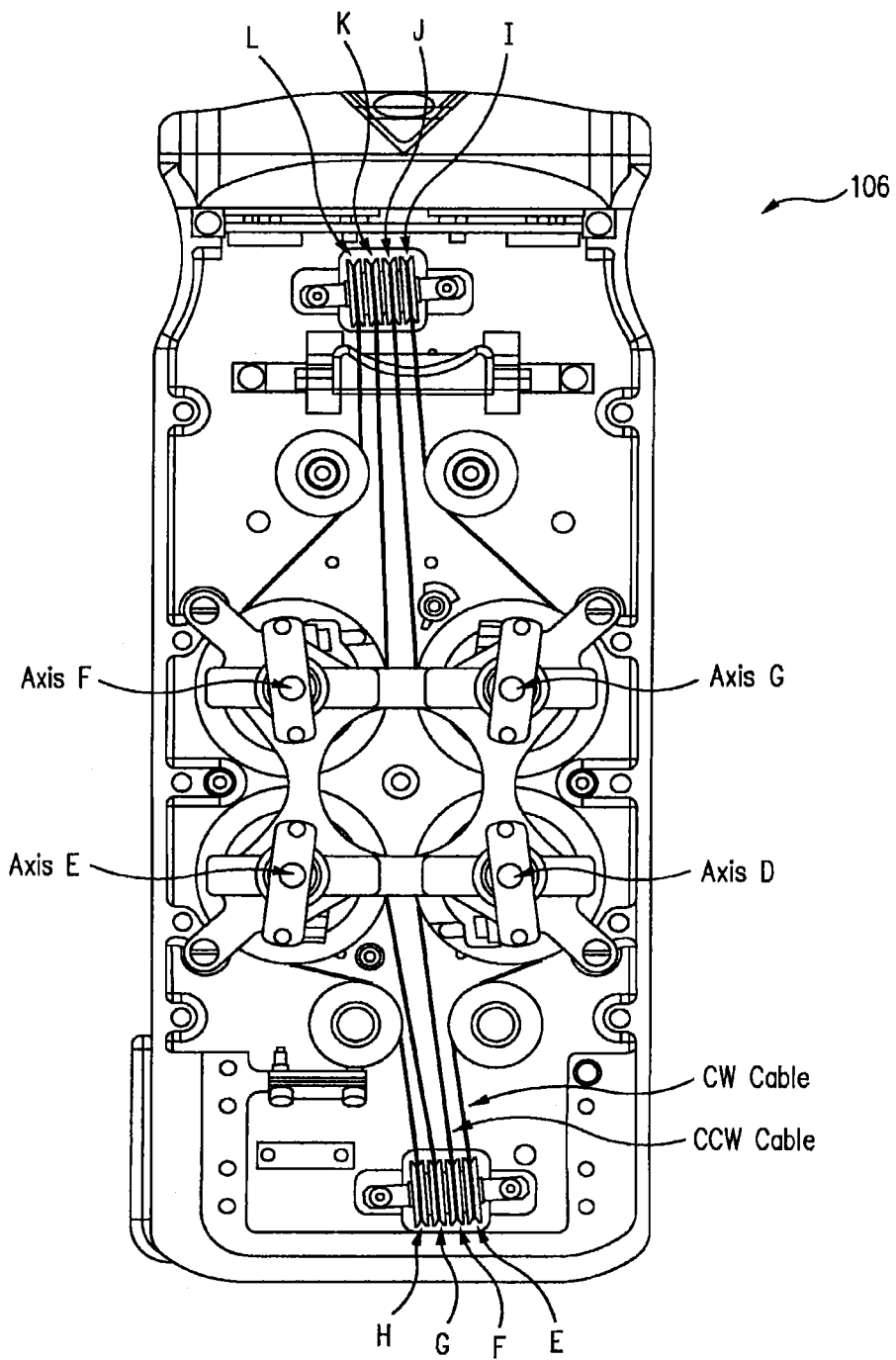

The first type of cable shall be referred to as an insertion cable (e.g., cables 121 and 122 of FIGS. 11A and 11B). The function of these cables is to position the insertion axis. In this particular embodiment there are two insertion cables: a cable 121 to retract the insertion axis and a cable 122 to extend the insertion axis. Furthermore, cables 121 and 122 are doubled over their respective termination points (e.g., termination points 131 and 132, respectively) to idler link 104 and routed back to the motor capstan (a pulley coupled to a motor) they originated from, thus providing redundancy in the cabling scheme. In these particular examples, cable 121 runs between a capstan and termination point 131 and along pulleys 141 and 142 for retracting the insertion axis, and cable 122 runs between a capstan and termination point 132 and along pulleys 143 and 144 for extending the insertion axis. Cables 121 and 122 may move along other pulleys as well. This cable configuration or drive scheme for controlling the position of idler link 104 yields a 2:1 mechanical coupling with carriage link 106 in one example. In other words, the output (e.g., carriage link 106) moves twice as much as the input (e.g., idler link 104).

In another example, as illustrated in FIGS. 11C and 11D, insertion cables 123 and 124 may be terminated (e.g., at termination points 133 and 134, respectively) directly to the output of the linear stage, which is carriage link 106. This drive scheme yields a 1:1 mechanical coupling between the drive and output. In these particular examples, cable 123 runs between a capstan and termination point 133 and along pulleys 145 and 146 for retracting the insertion axis (i.e., for driving the carriage link down toward the base link), and cable 124 runs between a capstan and termination point 134 and along pulleys 147 and 148 for extending the insertion axis (i.e., for driving the carriage link up away from the base link). Cables 123 and 124 may move along other pulleys as well.

In yet another example, the insertion cables can be looped over idler link 104 and terminated onto base link 102, and the resulting mechanical coupling ratio would still be 1:1. Other cabling configurations or drive schemes that yield different mechanical coupling ratios are within the scope of the present invention.

Figure 11E:
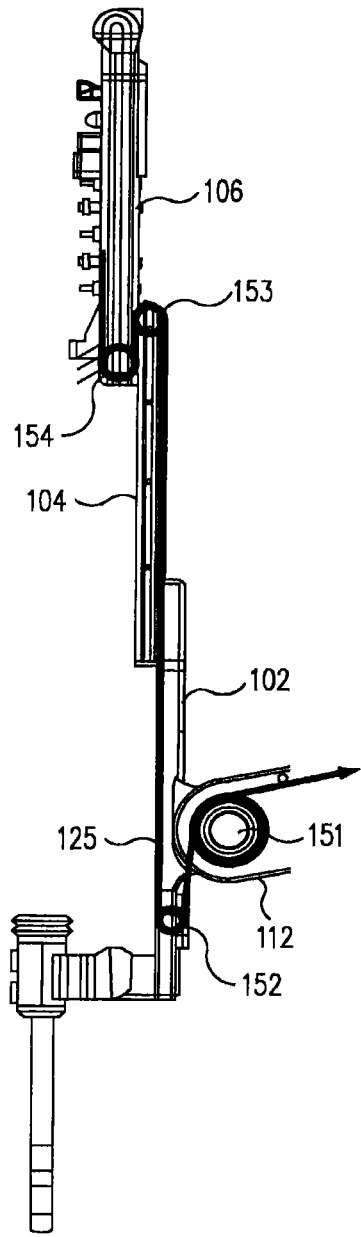
Figure 11F:
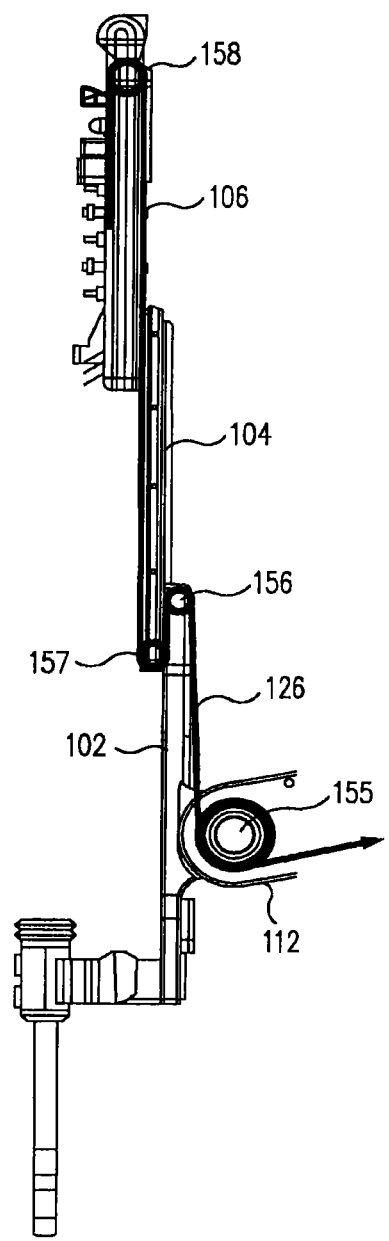

The second type of cable shall be referred to as a wrist cable (e.g., cables 125 and 126 of FIGS. 11E and 11F). These cables comprise the drivetrain of axes D through G (FIGS. 5A, 5A1, and 12C), with FIG. 11E illustrating a cable path for wrist axes D and E and FIG. 11F illustrating a cable path for wrist axes F and G in one example. The wrist cables have two primary functions in the telescopic insertion axis. In one example, the wrist cables control the four output axes on carriage link 106, which in turn control the surgical instruments operably coupled to the carriage link. In another example, the wrist cables are routed between the three links in such a way that they provide the mechanical means for the links to move relative to one another in a telescopic fashion. Furthermore, the routing of the wrist cables is such that the wrist axes are mechanically decoupled from the insertion axes. In other words, a change in position of one axis does not affect the position of any other axis; yet, their drivetrains are shared.

To further explore this decoupling, the wrist cable paths between base link 102 and carriage link 106 will be described. As the wrist cables leave pulley bank 112 on the rear of base link 102, there are two basic paths the wrist cables may follow to carriage link 106. One cable path leads into a lower side of carriage link 106 (FIG. 11E), and the other cable path leads into a top side of carriage link 106 (FIG. 11F). In these particular examples, cable 125 runs between a capstan and wrist axis D or E along pulleys 151, 152, 153, and 154 for controlling a coupled instrument, and cable 126 runs between a capstan and wrist axis F or G along pulleys 155, 156, 157, and 158 for controlling a coupled instrument. Cables 125 and 126 may move along other pulleys as well.

There are two cables per wrist axis, and these can be referred to as the CW and CCW cables since each cable is used to spin the output pulley in either a clockwise or a counterclockwise direction. Focusing on the axis D cables, which enter carriage link 106 from a lower side (FIG. 11E), the axis D CW and CCW cables run parallel to each other, as shown in FIG. 12C. Both the CW and CCW cables are attached to the same motor and capstan (not shown), and it is this motor that pulls the cables in either direction to position the output pulley as desired.

The motor drive capstan is the only influence on the position of the output pulley. The portion of the cable path between the base link 102 and carriage link 106 is of fixed length regardless of the position of idler link 104. Since the two drive cables for each of the wrist axes run in parallel to each other between base link 102 and carriage link 106, forces that result from the motion of idler link 104 over the other links has substantially an equal effect on both cables, thus substantially canceling out any net effect on the output pulleys. Thus, motion of the insertion cables and forces on links 102, 104, and 106 have substantially no effect on the position of the wrist axes cables.

Furthermore, this fixed length of cable between base link 102 and carriage link 106 also provides the necessary drivetrain for carriage link 106 to move relative to idler link 104, therefore enabling the telescopic motion of insertion axis 100. In particular, the relative motion between carriage link 106 and idler link 104 is substantially the same as the relative motion between base link 102 and idler link 104. Therefore, the net displacement of carriage link 106 relative to base link 102 is twice that of idler link 104 relative to base link 102, thus allowing for the telescopic motion of the insertion axis from a fully retracted position to a fully extended position.

In yet another example of the present invention, the motion of the wrist axes cables also does not influence the position of the insertion axes cables. Forces that result from the motion of a set of parallel wrist axis cables are reacted (i.e., the necessary reaction force is provided) in the wrist cables on the opposite side of carriage link 106. In particular, axis D and E cable forces are reacted by axis F and G cables, respectively, and vice versa. The stiffness of the wrist cables is sufficiently high to prevent unwanted motion of the insertion axis. Also, the cable forces required to drive the wrist axes are sufficiently low to not cause unwanted motion of the insertion axis.

The free end of cables 121-126 may be operably coupled to capstans operably coupled to a motor (or a plurality of motors) (not shown) for actuating the cables. The motor may be mounted remotely from the insertion axis, thus allowing the motor to be mounted in a location where its size and weight have a minimal negative effect on the functionality of the insertion axis or surgical robot.

FIGS. 12A-12C illustrate views of links 102, 104, and 106 showing cables A through L. Between FIGS. 11A-11F and FIGS. 12A-12C, the cables may be mapped as follows: cable 121 correlates to cables B and D; cable 122 correlates to cables A and C; cable 123 correlates to cables B and D; cable 124 correlates to cables A and C; cable 125 correlates to cables E, F, G, and H; and cable 126 correlates to cables I, J, K, and L.

Although certain drivetrains have been described above, other means and methods for providing a telescoping action for the insertion axis are applicable. In one example, short cables may be looped between the links of the insertion axis to provide telescoping movement in a synchronized fashion. Sections of cable could be terminated on the base link, routed through the idler link, and terminated on the carriage link, with loops being provided for both "up" and "down" directions. In another example, the telescoping action could be achieved using a rack and pinion system, with racks on the face of the base link, racks on the back of the carriage link, and a rotating pinion riding on the idler link.

To get power and signals to and from a printed circuit assembly (PCA) in carriage link 106, a wire harness may be used. In one embodiment, the remote PCA may have inputs and outputs for providing power and/or communicating with LEDs, Hall effect sensors, a sterile adaptor, an instrument, and a user interface button (e.g., for a clutch operation). The remote PCA may also include an input for receiving power and an input/output for communicating with a main PCA (e.g., processor 4 of FIG. 1). In one embodiment, the main PCA may have inputs and outputs for providing power and/or communicating with motors (e.g., the main PCA transmits position controls to the motors and processes potentiometer and encoder signals), sensors, the user interface button, the remote PCA, and other printed circuit boards on a patient side cart system via a serial communication bus. An example of the inputs and outputs of applicable PCAs are described in U.S. application Ser. No. 11/613,915, filed Dec. 20, 2006, entitled "Wireless Communication In A Robotic Surgical System", the complete disclosure of which has been previously incorporated herein by reference for all purposes. The remote PCA may include, in one example, an Embedded Serializer for Instrument Interface (ESII) PCA, and the main PCA may include, in one example, an Embedded Serializer Patient Manipulator (ESPM) PCA, both of which are available from Intuitive Surgical, Inc. of Sunnyvale, Calif.

Figure 13A:
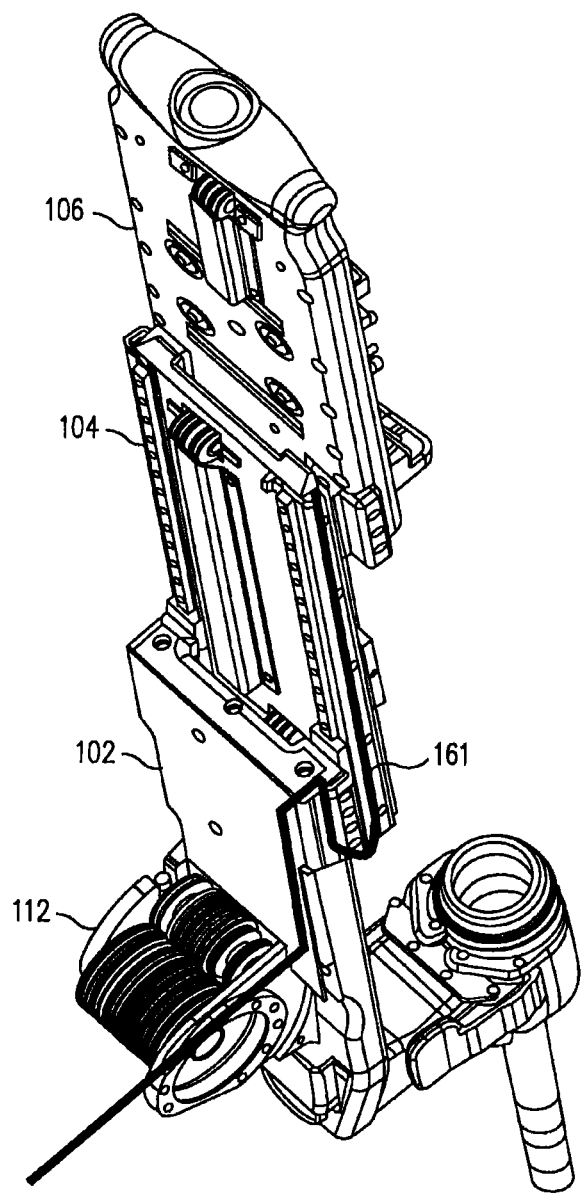
FIGS. 13A-13B illustrate views of electrical wire harnesses of the insertion axis in accordance with an embodiment of the present invention.
Figure 13B:
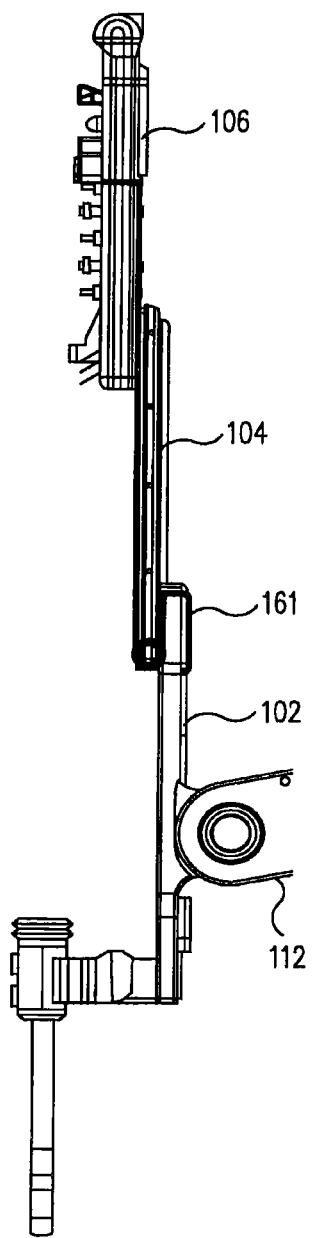

The simplest path for this harness between base link 102 and carriage link 106 is similar to the cable paths previously described. An example of a wire harness pathway is illustrated in FIGS. 13A and 13B. Advantageously, in one embodiment, the length of the wire harness pathway is fixed between base link 102 and carriage link 106 regardless of the position of idler link 104.

To meet the specific requirements of this application, a flat flexible cable (FFC) 161 was chosen. FFCs can fit many conductive paths into a small size, and they have superb bending performance. That is, they can survive millions of cycles of bending around relatively small radii.

One potential issue with FFCs is that they are not particularly robust when subjected to external forces. To protect the FFC from external damage, a thin cover may be placed over the exposed surface of the FFC. This cover may be made from a thin strip of high strength stainless steel in one example. Other materials are also applicable.

Another use of the FFC 161 rolling loop is to establish a ground path between base link 102 and carriage link 106. External conductive parts of a surgical robot must be connected to electrical ground with sufficiently low impedance per UL 60601. The ground path through the mechanical hardware between base link 102 and carriage link 106 may not be sufficient to meet UL 60601 requirements. In one example, extra FFCs may be clamped to each link to provide the extra conductive paths needed to meet the UL standard. These FFCs run in parallel with the FFC used for carrying power and signals to the PCA in carriage link 106. An alternative solution to the ground problem is to use sliding wipers between links 102 and 104 as well as between links 104 and 106. An example of sliding wipers is provided in U.S. application Ser. No. 11/613,915, filed Dec. 20, 2006, entitled "Wireless Communication In A Robotic Surgical System", the complete disclosure of which has been previously incorporated herein by reference for all purposes. Accordingly, the present invention provides a robust, low-resistance ground path across the links of the insertion axis.

Figure 14A:
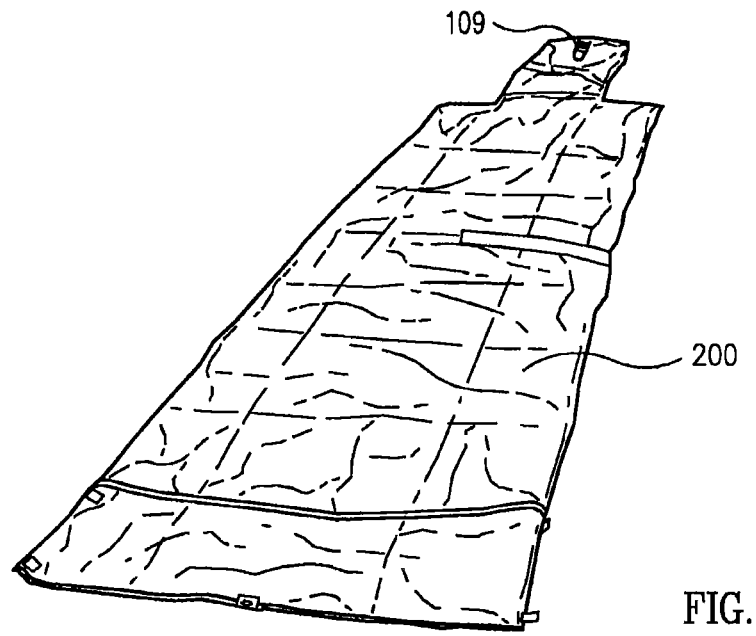
FIGS. 14A-14D illustrate a sterile drape for a portion of the manipulator system including the insertion axis in accordance with an embodiment of the present invention.
Figure 14B:
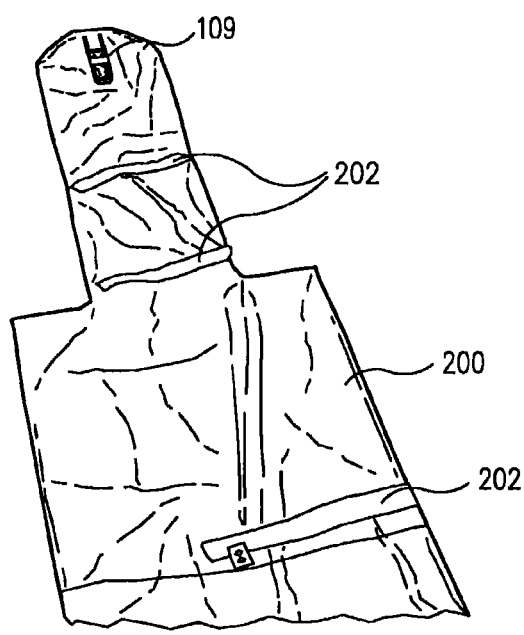
Figure 14C:
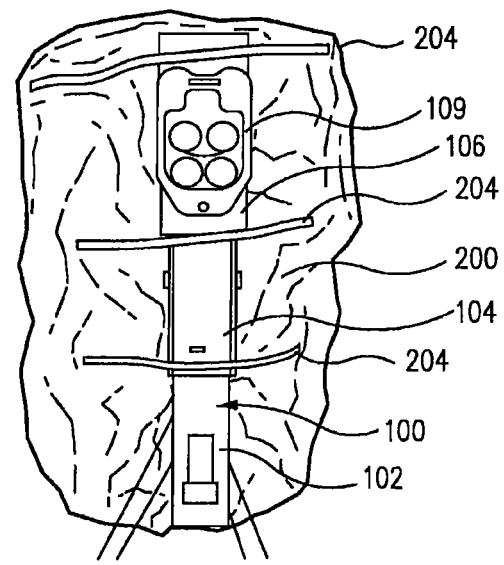
Figure 14D:
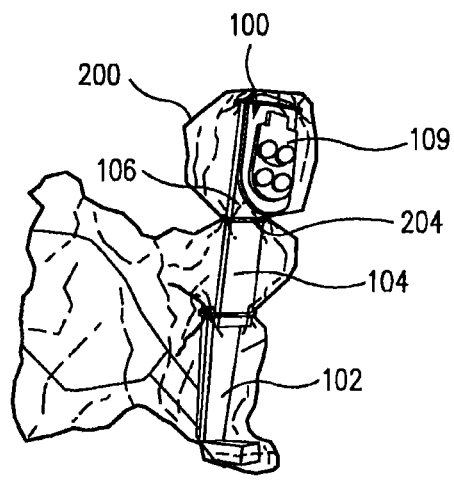

FIGS. 14A-14D illustrate a sterile drape 200 including a sterile adaptor 109 for draping a portion of the manipulator system of the present invention in accordance with an embodiment of the present invention. FIGS. 14C and 14D illustrate the sterile drape 200 positioned over the insertion axis 100 and adaptor 109 operably coupled to instrument interface 101 of carriage link 106 in accordance with an embodiment of the present invention. An example of an applicable drape is disclosed in pending U.S. application Ser. No. 11/240,113, filed Sep. 30, 2005, the full disclosure of which is incorporated by reference herein for all purposes. The PSM drape 200 is designed to establish a sterile barrier between the non-sterile PSM arms and the sterile field of the surgical procedure. PSM drape 200 includes an integral instrument sterile adaptor (ISA) 109 permanently mounted on the drape in one embodiment. Thus, the drape is completely disposable in one example.

Advantageously, various features of the PSM drape aid the draping and installation process. In one example, drape 200 includes tear strips which allow for the controlled unfolding of the drape by tearing when pulled on with the necessary force, integral cuffs for pulling the PSM drape along the PSM arm, and straps 202 and strips 204 to help control the drape and reduce the visual size of the drape (i.e., reduce the volume of or space taken up by the unfolded drape). One strap may be proximate the cannula mount area, another strap may be proximate the insertion link of the PSM arm, and another strap may be along a setup arm onto which the PSM arm is mounted. Strips 204 along the insertion axis are malleable strips which the user can deform to help fold back excess drape material around the insertion axis. By being able to fold back and secure excess drape material, the drape can be made to closely fit the shape of the PSM arm, thus reducing the visual size of the system and thereby allowing more visibility of the patient and their surroundings to the surgeon or other user(s). Strips 204 are also sufficiently malleable to be able to open up to allow the system to achieve maximum range of motion without tearing the drape and also to be reshaped by the user as desired during the procedure.

FIG. 14D shows PSM drape 200 over the insertion axis 100 and sterile adaptor 109 in place prior to strips 204 being bent back by the user. FIG. 14D shows strips 204 after being bent back by the user such that PSM drape 200 more closely fits the shape of the PSM arm, thereby reducing the visual size of the system.

Drape 200 as described above is preferably comprised of material of sufficient rigidity and strength to allow proper placement over a PSM arm and to resist tearing even under application of cyclical loads in various directions, but are preferably comprised of material of sufficient flexibility to allow movement with the active sections of the manipulator arms.

Figure 15:
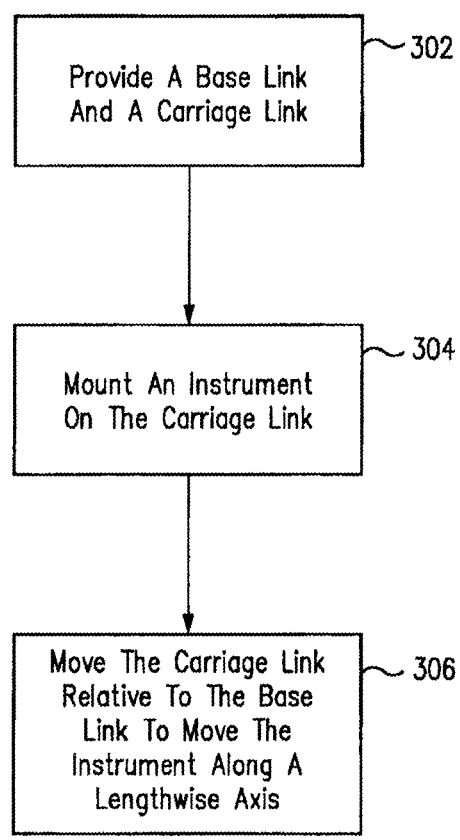
FIG. 15 is a flowchart of a method for using the manipulator system in accordance with an embodiment of the present invention.

Referring now to FIG. 15, a flowchart of a method for using the manipulator system is shown in accordance with an embodiment of the present invention. At step 302, an insertion axis of a robotic surgical system is provided, the insertion axis including a carriage link movably coupled to a base link. At step 304, an instrument is mounted onto the insertion axis, in particular the carriage link including an instrument interface, and the base link including a mounting portion. At step 306, the carriage link is moved relative to the base link, in particular in a telescoping fashion, to linearly move the mounted instrument. The wrist axes of the instrument are controlled by spinning of the wrist axes D through G.

Cooperative telesurgical systems which may be modified to take advantage of the telescopic insertion axis of the present invention is described in more detail in U.S. Pat. No. 6,659,939, the full disclosure of which is incorporated herein by reference.

Embodiments described above illustrate but do not limit the invention. It should also be understood that numerous modifications and variations are possible in accordance with the principles of the present invention. For example, although the insertion axis described above includes three links operably coupled to one another, the number of links may vary. In particular, the insertion axis of the present invention may include two or more links (e.g., four or more) movably coupled to one another allowing for telescopic movement relative to one another. Furthermore, the system is not limited to four robotic manipulator assemblies, but may include two or more in other examples. In addition, the present invention is not limited to four wrist axes but may include two or more in other embodiments. Accordingly, the scope of the invention is defined only by the following claims.

The invention claimed is:

1. A link assembly comprising:
    a base link operably coupled to a distal end of a manipulator arm;
    an idler link movably coupled to the base link along a lengthwise axis of the link assembly, the idler link having first and second opposite surfaces;
    a carriage link movably coupled to the idler link along the lengthwise axis, wherein the carriage link includes an instrument interface;
    a first linear bearing mounted to the first surface of the idler link;
    a second linear bearing mounted to the second surface of the idler link; and
    a first pressure plate mounted to the idler link, the first pressure plate clamping the first and second linear bearings to the first and second opposite surfaces of the idler link, respectively.

2. The link assembly of claim 1, further comprising a pair of shoulder projections extending from each of the first and second opposite surfaces, respectively, wherein first and second linear bearings are each clamped between the first pressure plate and one of the pair of shoulder projections.

3. The link assembly of claim 1, wherein the first and second linear bearings each include a linear rail and a slide unit slidably mounted to the linear rail.

4. The link assembly of claim 3, wherein each linear rail is fixedly clamped between the idler link and the first pressure plate.

5. The link assembly of claim 3, wherein the slide unit of the first linear bearing is mounted to the base link such that the base link is translatable along the linear rail of the first linear bearing.

6. The link assembly of claim 3, wherein the slide unit of the second linear bearing is mounted to the carriage link such that the carriage link is translatable along the linear rail of the second linear bearing.

7. The link assembly of claim 1, wherein the first pressure plate provides a clamping force parallel to first and second opposite surfaces of the idler link.

8. The link assembly of claim 1, further comprising:
a third linear bearing mounted to the first surface of the idler link;
a fourth linear bearing mounted to the second surface of the idler link; and
a second pressure plate mounted to the idler link, the second pressure plate clamping the third and fourth linear bearings to first and second opposite surfaces of the idler link, respectively.

9. The link assembly of claim 8, wherein the third and fourth linear bearings each include linear rail and a slide unit slidably mounted to the linear rail.

10. The link assembly of claim 9, wherein the first linear bearing is parallel to the third linear bearing and the second linear bearing is parallel to the fourth linear bearing and wherein a distance between the first and third linear bearings is smaller than a distance between the second and fourth linear bearings.

11. A telesurgical manipulator system comprising:
a manipulator assembly including:
  a base link operably coupled to a distal end of a manipulator arm;
  an idler link movably coupled to the base link along a lengthwise axis of the link assembly, the idler link having first and second opposite surfaces;
  a carriage link movably coupled to the idler link along the lengthwise axis, wherein the carriage link includes an instrument interface;
  a first linear bearing mounted to the first surface of the idler link;
  a second linear bearing mounted to the second surface of the idler link; and
  a first pressure plate mounted to the idler link, the first pressure plate clamping the first and second linear bearings to the first and second opposite surfaces of the idler link, respectively;
an instrument coupled to the carriage link via the instrument interface; and
a processor operably coupled to the manipulator assembly and configured to move the base, idler, and carriage links relative to one another along the lengthwise axis.

12. The system of claim 11 further comprising a pair of shoulder projections extending from each of the first and second opposite surfaces of the idler link, respectively, wherein first and second linear bearings are each clamped between the first pressure plate and one of the pair of shoulder projections.

13. The system of claim 11 wherein the first and second linear bearings each include a linear rail and a slide unit slidably mounted to the linear rail.

14. The system of claim 13 wherein each linear rail is fixedly clamped between the idler link and the first pressure plate.

15. The system of claim 13 wherein the slide unit of the first linear bearing is mounted to the base link such that the base link is translatable along the linear rail of the first linear bearing.

16. The system of claim 13 wherein the slide unit of the second linear bearing is mounted to the carriage link such that the carriage link is translatable along the linear rail of the second linear bearing.

17. The system of claim 11 wherein the first pressure plate provides a clamping force parallel to first and second opposite surfaces of the idler link.

18. The system of claim 11 further comprising:
a third linear bearing mounted to the first surface of the idler link;
a fourth linear bearing mounted to the second surface of the idler link; and
a second pressure plate mounted to the idler link, the second pressure plate clamping the third and fourth linear bearings to first and second opposite surfaces of the idler link, respectively.

19. The system of claim 18 wherein the third and fourth linear bearings each include linear rail and a slide unit slidably mounted to the linear rail.

20. The system of claim 19 wherein the first linear bearing is parallel to the third linear bearing and the second linear bearing is parallel to the fourth linear bearing and wherein a distance between the first and third linear bearings is smaller than a distance between the second and fourth linear bearings.

* * * * *